United States Patent
Sprott et al.

(10) Patent No.: US 6,403,117 B1
(45) Date of Patent: *Jun. 11, 2002

(54) ARCHAESOMES, ARCHAEOSOMES CONTAINING COENZYME $Q_{10}$ AND OTHER TYPES OF LIPOSOMES CONTAINING COENZYME $Q_{10}$ ADJUVANTS AND AS DELIVERY VEHICLES

(75) Inventors: G. Dennis Sprott, Orleans; Girishchandra B. Patel, Nepean; Boby Makabi-Panzu, Gatineau, all of (CA)

(73) Assignee: National Research Council of Canada, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/612,618

(22) Filed: Jul. 6, 2000

Related U.S. Application Data

(62) Division of application No. 09/077,956, filed as application No. PCT/CA96/00835 on Dec. 13, 1996, now Pat. No. 6,132,789.
(60) Provisional application No. 60/008,724, filed on Dec. 15, 1995.

(51) Int. Cl.[7] .................................................. A61K 9/127
(52) U.S. Cl. ................. 424/450; 424/184.1; 424/193.1; 424/204.1; 424/94.3; 424/812; 424/1.21; 424/9.321; 424/9.51; 935/54; 436/829
(58) Field of Search .............................. 424/450, 184.1, 424/193.1, 812, 1.21, 9.32, 9.51, 197.11, 204.1, 94.3; 436/829; 935/54

(56) References Cited

U.S. PATENT DOCUMENTS

| 4,636,381 A | 1/1987 | Takada |
| 4,743,449 A | 5/1988 | Yoshida |
| 5,034,228 A | 7/1991 | Meybeck |

FOREIGN PATENT DOCUMENTS

| WO | 93/08202 | 4/1993 |

OTHER PUBLICATIONS

Allen, BBA, 1066, pp. 29–36, 1991.
Phillips, Cancer Detection and Prevention, 14, #4, pp. 491–496, 1990.
Wassef, Immunomethods, 4, pp. 217–222, 1994.
Alving, Vaccine 4, pp. 166–172, 1986.
Shek Biochimica et Biophysica Acta 855 (1986) 33–40 Physiochemical and immunological properties etc.

*Primary Examiner*—Gollamudi S. Kishore
(74) *Attorney, Agent, or Firm*—Nixon & Vanderhye

(57) ABSTRACT

Novel archaeosome compositions and their use in vaccine formulations as adjuvants and/or delivery systems, to enhance the immune response to immunogens in an animal such as a human, are described. Another aspect relates to the use of these archaeosomes to enhance the delivery of compounds such as pharmaceuticals to specific cell types and tissues in animals and other life forms, via various routes of administration such as subcutaneous, intramuscular, and oral. The efficacy of the archaeosomes and also of conventional liposomes can be further improved in these applications, by incorporation of coenzyme $Q_{10}$ and/or polyethyleneglycol-lipid conjugate into liposomes made from these archaeosomes.

24 Claims, 10 Drawing Sheets

ARCHAESOMES, ARCHAEOSOMES CONTAINING COENZYME $Q_{10}$ AND OTHER TYPES OF LIPOSOMES CONTAINING COENZYME $Q_{10}$ ADJUVANTS AND AS DELIVERY VEHICLES

This application is a division of Ser. No. 09/077,956 filed Jun. 12, 1998, which was based on PCT/CA96/00835 filed Dec. 13, 1996 now U.S. Pat. No. 6,132,789 which claims benefit over No. 60/008,724 filed Dec. 15, 1995.

FIELD OF THE INVENTION

This invention relates to liposomes (closed lipid vesicles) made from archaeobacterial lipids, from non-archaeobacterial lipids, and mixtures thereof, and to the use of such liposomes for the enhanced delivery of pharmaceutical and other compounds to specific cell types such as macrophages/phagotocytes/antigen processing cells and to specific tissues in life-forms such as humans, and for the enhancement of the immune response to antigen(s) presented to a life-form such as a human. The vesicles of this invention may be used in vaccine formulations after encapsulation of, or in conjunction with, one or more immunogen, with or without mediation by the presence of other adjuvants or compounds. The invention may also be used, without limitations, for delivery of drugs, antibiotics, pharmaceuticals, biological compounds such as enzymes or DNA or hormones, therapeutics, imaging agents etc to specific cell types or specific tissues in an animal such as a human and other life-forms. Another application may be to use antibiotics/antiviral agents encapsulated in archaeosomes to treat diseases, where the infective organisms may reside as intracellular reservoirs (such as in macrophages) for re-infection.

DESCRIPTION OF THE PRIOR ART

Liposomes are closed lipid vesicles containing an entrapped aqueous volume. The hydrophilic head groups of the lipids forming liposomes are oriented towards the aqueous environments present inside and outside the liposomes, whereas the hydrophobic regions of the lipids are sandwiched between the polar head groups and away from the aqueous environments. Liposomes may be unilamellar containing a single lipid bilayer, or multilamellar containing multiple bilayers (onion-like in structure) with an aqueous space separating each bilayer from the other. Various techniques for forming liposomes have been described in the literature, including but not limited to, pressure extrusion, detergent dialysis, dehydration-rehydration, reverse-phase evaporation, remote loading, sonication and other methods (13). Liposomes made from conventional ester phospholipids such as phosphatidylcholine are referred to herein as conventional liposomes, even if they contain sterols or other compounds in their bilayer.

Liposomes consisting of a lipid bilayer, a monolayer or a combination thereof, made from any lipid(s) which include in their composition ether lipids extracted from or found in Archaeobacteria, or those synthesized to mimic lipids found in archaeobacteria, are referred to herein as archaeosomes.

Archaea (Archaeobacteria) are considered to be distinct from eubacteria and eukaryotes, and they include aerobic, anaerobic, thermophilic, extremely thermophilic, thermoacidophilic, and halophilic microorganisms. Total lipid extracts from individual species of Archaea consist of polar ether lipids and from 5 to 20% neutral lipids. The polar ether lipids of Archaea consist of branched phytanyl chains which are usually saturated and are attached via ether bonds to the glycerol carbons at the sn-2,3 positions (8). In contrast to this, in conventional phospholipids found in Eubacteria and Eukaryotes, fatty acyl chains which may be unsaturated, are attached via ester bonds to the sn-1,2 carbons of the glycerol backbone. The core structures of the archaeobacterial ether lipids (the polar head groups removed by hydrolysis) consist of the standard diether lipid (2,3-di-O-phytanyl-sn-glycerol or archaeol), and the standard tetraether lipid (2,2',3,3'-tetra-O-dibiphytanyl-sn-diglycerol or caldarchaeol) and modifications thereof (8). Diether lipids are monopolar like the conventional phospholipids, whereas the tetraether lipids are bipolar. The polar head groups, attached to the sn-1 glycerol carbon in the diethers and to the sn-1 and sn-1' glycerol carbons in the tetraethers, can vary and may include phospho groups, glyco groups, phosphoglyco groups, polyol groups, c hydroxyl groups (18). In contrast to the phosphatidylcholine conventional lipid commonly used in liposome formulations, the phosphocholine head group is very rarely found in archaeobacterial polar lipids. Archaea provide a large selection of lipids to screen for the preparation of vesicles having the properties useful for specific applications, and overcome the difficulties associated with conventional lipids such as low adjuvanticity and instability.

There is much interest in the use of liposomes for medical, pharmaceutical, and other commercial applications. Most of the research reported on liposomes to-date, has been conducted using conventional phospholipids sometimes mixed with sterols (e.g., cholesterol) or other compounds to improve stability, rather than using either archaeobacterial or non-archaeobacterial ether lipids.

In a comparative study on the uptake of liposomes made with 1,2-diacyl-sn-glycero-3-phosphocholine and its ether analog, by cultured rat liver hepatocytes, the cellular uptake of both liposome types was found to be similar (21). In another study, liposomes made with either dipalmitoyl phosphatidylcholine or its ether analogue 1-O-octadecyl-2-O-methyl-rac-glycerol-3-phosphocholine, were phagocytosed at about the same rate by J774.E1 macrophage cells (6). Therefore, from these disclosures it would be expected that liposomes made with ether lipids, including by extension those from ether lipids either extracted from Arcaea or from ether lipids chemically synthesized to mimic the unique lipid structures of Archaea, would be taken up by certain cells such as macrophages, to a similar extent as conventional liposomes. However, the current invention proves to the contrary, showing enhanced phagocytosis of vesicles (archaeosomes) made with archaeobacterial ether lipids.

Intracellular delivery of antibiotics and other drugs to control pathogens which reside within certain cell types such as macrophages is a current problem, e.g., the bacterium *Mycobacterium tuberculosis* which causes tuberculosis, viruses such as the human immunodeficiency virus (HIV) which causes acquired immune deficiency syndrome (AIDS), and parasites which cause malaria. A superior uptake of archaeosomes made with ether lipids of Archaea would have commercial utility in enhancing the delivery of drugs, antigens, and other compounds targeted for delivery to phagocytic cells of a life-form, such as a human.

There is considerable interest in the potential use of liposomes in the field of vaccine applications. Liposomes prepared from conventional phospholipids, sometimes mixed with cholesterol or other compounds (conventional liposomes) have been tested as potential antigen carriers/vehicles. Allison and Gregoriadis (1) reported that liposomes prepared from egg phosphatidylcholine had some adjuvant activity, provided a negatively charged lipid was included in the liposome composition. Since conventional liposomes often demonstrate only small adjuvant effects as compared with administration of the free antigen, various immunostimulatory substances such as lipid A have been co-incorporated into the liposomes, together with the antigen (4). However, as is the case with lipid A and Freund's adjuvant, immunostimulatory substances may have toxicity associated problems, making them unsuitable for vaccine applications.

The humoral immune response, in mice, to bovine serum albumin encapsulated in liposomes made with dialkyl-ether sn-3-phosphatidylcholine was lower than that obtained with similar liposomes made with diacyl-ester sn-3 phosphatidylcholine (17). There is no teaching in the prior art to suggest true compared with liposomes made using conventional phospholipids, those made using archaeobacterial ether lipids would have a superior adjuvant effect in stimulating the immune response to an antigen administered into an animal by various routes (including but not limited to intramuscular (i.m.), intravenous (i.v.), intraperitoneal (i.p.), subcutaneous (s.c.), and peroral(p.o.)).

Coenzyme $Q_{10}$ (also known as $CoQ_{10}$, ubiquinone-10 or ubidecarenone-10) is present in mammalian cells having mitochondria where it is a redox component in the respiratory chain. Since decreased levels of $CoQ_{10}$ have been implicated in certain pathological conditions such as myocardiac insufficiency, cardiac infarction, muscular dystrophy, arterious hypertension, and in the symptoms of ageing, it has been considered for therapeutic applications in such cases. Deficiency of $CoQ_{10}$ has also been reported in AIDS patients (5). $CoQ_{10}$ is extremely hydrophobic in nature and unless its chemical structure is artificially modified, it is not soluble in aqueous buffers or water. Similarities are noted between $CoQ_{10}$ and vitamin E, with respect to serving as immune stimulators and as antioxidants. $CoQ_{10}$ as an emulsion with detergents has been shown to enhance the in vivo phagocytic activity in animal models (3). Labelled $CoQ_{10}$ has been used in conventional liposomes as a marker for myocardial imaging and for studying tissue distribution of conventional liposomes coated with polysaccharides (7,22). In liposomes, $CoQ_{10}$ is associated with the lipid layer of the vesicles. However, none of these or other prior art publications teach that the combination of $CoQ_{10}$ in archaeosomes would enhance the phagocytosis of the resultant vesicles by macrophage cells (compared to that of the archaeosomes without $CoQ_{10}$), or that such a combination would allow the alteration in targeting profiles to specific tissues when the vesicles are administered to an animal via different routes, or that such combinations would further enhance the immune response to co-administered immunogen(s) (current claimed invention). Similarly, the prior art does not teach that the combination of $CoQ_{10}$ in conventional liposomes would increase the phagocytosis of the resultant liposomes by macrophages, or allow for the alteration of tissue targeting profiles when the liposomes are administered to an animal by different routes, or that liposomal $CoQ_{10}$ combination would enhance the immune response to co-administered immunogen(s) compared to the liposomal immunogen in the absence of $CoQ_{10}$.

SUMMARY OF THE INVENTION

It is an object of this invention to use archaeosomes as beneficial carriers of antigens, immunogenic compounds, DNA, drugs, therapeutic compounds, pharmaceutical compounds, imaging agents or tracers, and to deliver these to specific cells such as the macrophages or to specific tissues, in life-forms such as the human.

It is a further object of this invention to provide archaeosomes that have enhanced adjuvant activity for the generation of an immune response to an immunogen, and for vaccine applications in an animal such as a human, wherein the antigen(s) can be encapsulated in, can be associated with, or not associated with the archaeosomes, at the time of administration via different routes. In some instances the immune response (the level of response and its duration) to an immunogen delivered via an archaeosome being comparable to that obtained with Freund's adjuvant as the immunostimulator.

Yet another object of the invention is to use archaeosomes prepared with lipids containing a high proportion of tetraether bipolar lipid(s) that are found in, or mimic those found in, members of archaeobacteria, to enhance and prolong the immune response to an immunogen that is either codministered as part of the archaeosome or administered at the same time as the archaeosome, into an animal.

It is another object of the invention to incorporate coenzyme $Q_{10}$ into archaeosomes, or into liposomes prepared exclusively from lipids other than archaeobacterial-like ether lipids, to enhance the phagocytosis of the respective archaeosomes/liposomes, and/or to enhance the delivery of $CoQ_{10}$ as well as other associated drug(s), and to enhance the immune response to an antigen associated with the respective archaeosomes/liposomes.

It is another object of this invention to incorporate $CoQ_{10}$ into archaeosomes and conventional liposomes, sometimes in combination with polyethylene glycol lipid conjugates, to increase the delivery of various associated compounds to specific organ tissues when the respective vesicles are administered to an animal via various routes such as p.o., i.m., i.v., s.c, and i.p. The combination of $CoQ_{10}$ in archaeosomal or conventional liposomal vesicles, including vesicles that may have been sterically stabilized by association with polyethyleneglycol conjugates, would therefore further increase the utility of archaeosomes and of conventional liposomes, for delivery of compounds, including immunogens and $CoQ_{10}$ itself, to phagocytic cells and to specific tissues.

It is yet another object of the invention to incorporate optimal amounts of archaeobacterial ether lipid(s) into mixtures with conventional lipids to prepare vesicles that have the above improved characteristics.

All of the above aspects of the current invention are interrelated in concept.

DETAILED DESCRIPTION OF PREFERRED EMBODIMENTS

Figure 1:
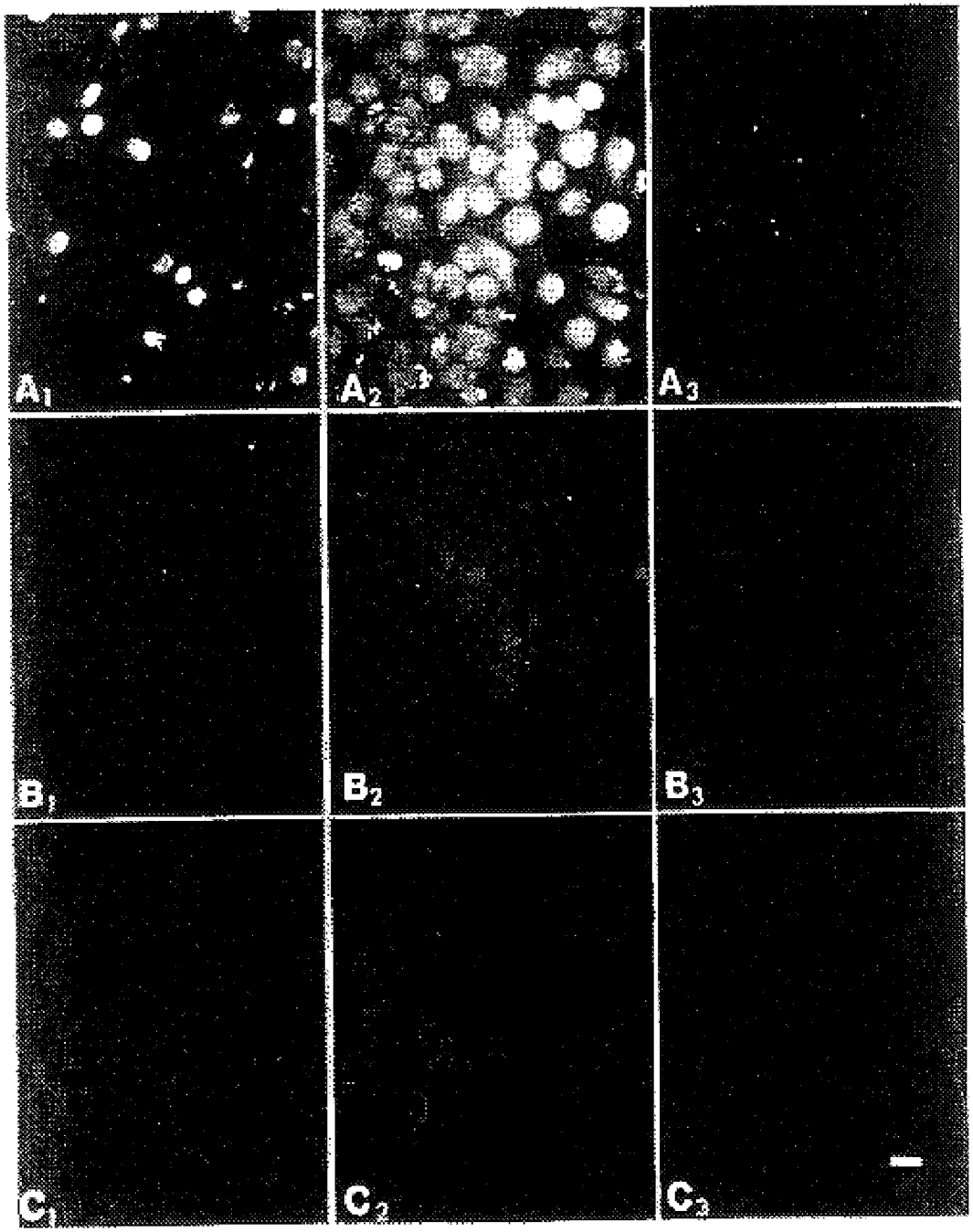
FIG. 1. Fluorescence micrographs of cells incubated with *Methanosarcina mazei* archaeosomes, or with conventional liposomes prepared from DMPC:DMPG:CHOL, each vesicle type containing CF. Panels $A_1$, $B_1$, $C_1$, murine peritoneal macrophages. Panels $A_2$, $B_2$, $C_2$, J774A.1 macrophages. Panels A3, $B_3$, $C_3$, HEp-2 cells. Panels $A_{1-3}$, archaeosomes; Panels $B_{1-3}$, conventional liposomes; and panels $C_{1-3}$, cells without added vesicles. The presence of yellow-fluorescent liposomes are indicated in the black and white photos by light areas. Magnification bar=20 μm.

The Archaea (Archaeobacteria) produce many different polyether lipid structures that are useful for the production of vesicles (archaeosomes) that have unique properties. Of the available species of Archaea as a class of organisms, we chose several as illustrative examples, to encompass a broad spectrum of ether lipid structures; namely, *Halobacterium cutirubrum, Methanococcus mazei, Methanospirillum hungatei, Methanococcus jannaschii, Methanosphaera stadtmanae, Methanobrevibacter smithii, Methanococcus voltae, Thermoplasma acidophilum*, and *Methanobacterium espanolae*. In this invention archaeosomes are vesicles that are prepared with lipids that include in its composition ether lipids extracted from one or more members of the Archaea, or a lipid(s) that mimics ether lipid structure(s) found in members of Archaea, or from one or more ether lipid(s) purified in a biologically pure form from Archaea. It will also be appreciated that lipids (such as those made by chemical synthesis) that mimic those found in the Archaea could also be used to make archaeosomes for the purposes stated in the current invention.

The inventors have discovered that archaeosomes are taken up by phagocytic cells to a greater extent than are conventional liposomes. Another aspect of the invention shows the improved uptake by phagocytic cells of both conventional liposomes and of archaeosomes, through the incorporation of coenzyme $Q_{10}$ in the respective vesicles. Incorporation of $CoQ_{10}$ into conventional liposomes, and archaeosomes, also allows for the improved targeting of vesicles to specific tissues in the animal, for vesicles administered via different routes. $CoQ_{10}$-containing archaeosomes with polyethylene glycol also incorporated, are particularly effective in the targeting of orally administered vesicles for delivery to tissues of the spleen and liver. This would be especially applicable for oral delivery of vaccines. Further, archaeosomes in general, are shown to be superior, compared to conventional liposomes, as carriers of antigens, resulting in improved immune response to the antigen administered to an animal such as a human. Further, it is shown that archaeosomes act as superior adjuvants, compared to conventional liposomes, resulting in an increased immune response to an antigen administered to an animal such as a human. Also, the duration of the immune response, as measured by the antibody titre, can be prolonged by preparation of archaeosomes with lipids containing a high proportion of tetraether bipolar lipids. Finally, coenzyme $Q_{10}$, when used in the preparation of vesicles, is shown to improve the immune response to an antigen co-entrapped either in conventional liposomes and/or in archaeosomes.

This invention will be better understood from the data given under the heading "RESULTS AND DISCUSSION". The data therein are for illustrative purposes only and do not limit the scope of the claimed invention.

Definitions of the Various Terms used in this Description

Antigen, an immunogen to which an animal such as a human mounts an immune response; conventional phospholipid, a glycerolipid in which the hydrocarbon chains are linked to the glycerol backbone via ester bonds; ether lipid, a glycerolipid in which the hydrocarbon chains are linked to the glycerol backbone via ether bonds; archaeal or archaeobacterial lipid(s), lipid(s) derived from a member(s) of the class Archaea (synonymous to Archaeobacteria); liposome, closed vesicle made of lipid bilayer membranes which entrap an aqueous volume, the liposome may be unilamellar (one bilayer) or multilamellar (multiple bilayers, each separated from the adjoining one by aqueous spaces); conventional liposome, a liposome made with conventional phospholipids and in some cases including a sterol and may include other compounds that are entrapped within the vesicle or associated with the bilayer membrane; archaeosome, a lipid vesicle made with one or more of the ether lipids that are unique to the species in the class Archaea, including those vesicles made from any combination of lipids that include archaeobacterial ether lipid(s) in their composition, the vesicle layer of archaeosomes may be entirely in the form of a bilayer (if made exclusively with monopolar diether lipids or with lipid mixtures containing diether and other monopolar lipids), or a monolayer (if made exclusively with bipolar tetraether lipids), or a combination of mono and bilayers (if made with diether or other monpolar lipids and tetraether lipids); vesicle, liposome or archaeosome; bare antigen, antigen without adjuvant or vesicle; bare liposome/archaeosome, liposome or archaeosome without an associated antigen; adjuvant, a substance or material which when administered with an immunogen increases the immune reaction to that immunogen. The name of the archaeobacterium associated with the word archaeosome (e.g., *M. espanolae* archaeosome, or archaeosome of from *M. espanolae*) indicates that the archaeosome is made with lipids extracted from that specific archaeobacterium, and unless stated to the contrary, from the total polar lipids (TPL) extracted from that archaeobacterium.

Materials and Methods

Materials

Archaeobacterial cultures were *Methanospirillum hungatei* GP1 (DSM 1101 ), *Methanococcus jannaschii* JAL-1 (DSM 2661), *Methanococcus voltae* PS (DSM 1537), *Methanosarcina mazei* S-6 (DSM 2053), *Methanobrevibacter smithii* AL1 (DSM 2375), *Methanosphaera stadtmanae* MCB-3 (DSM 3091), *Methanobacterium espanolae* GP9 (DSM 5982), *Halobacterium cutirubrum* (DSM 669), and *Thermoplasma acidophilum* 122-1B3 (ATCC 27658). Cultures were cultivated according to Sprott et al. (20).

L-α-dipalmitoylphosphatidylcholine (DPPC), L-α-dimyristoylphosphatidylcholine (DMPC), L-α-dimyristoylphosphatidylglycerol (DMPG), distearoylphosphatidylcholine (DSPC), dicetylphosphate (DCP, i.e., dihexadecyl phosphate), cholesterol (CHOL) (all these were at least 99% pure), 5(6)-carboxyfluorescein (CF), Triton X-100, n-propyl gallate, peroxidase substrate 2,2'-azino-bis (3-ethylbenzthiazoline sulphonic acid), horseradish peroxidase (1380 Units/mg), fatty acid free bovine serum albumin (BSA), coenzyme $Q_{10}$, vitamin E, Freund's complete adjuvant (CFA), and Freund's incomplete adjuvant (IFA) were purchased from Sigma Chemical Co., Mo., USA Distearoylphosphatidylethanolamine-polyethylene glycol 5000 conjugate (DSPE-PEG) was purchased from Avanti Polar Lipids, Inc., Alabama. Cholera toxin B subunit, from *Vibrio cholerae*, was purchased from Calbiochem (La Jolla, Calif.). Cholesteryl [1-$^3$H] hexadecyl ether ($^3$H-chol), 52 Ci/mmole was purchased from Amersham Canada Ltd., Oakville, Ont. Silica gel G was from Macherey Nagel and Co., Duren, Germany. The LiposoFast system and 400 nm filters were from Avestin, Inc., Ottawa, Canada. n-octyl-β-glucopyranoside (OGP) was a product from Calbiochem. Fetal bovine serum (FBS), and all media components including DMEM and RPM1 media, were purchased from Gibco Life Technologies, Inc., Grand Island, N.Y. Radioactivity counting supplies were obtained from ICN Biomedicals Inc., Irvine, Calif. 0-chain polysaccharide prepared from *Escherichia coli* 0:157:H7 was a gift from Dr. M. B. Perry (16). Immunological reagents for antibody isotyping were from Isotec, distributed by CedarLane Laboratories (Homby, Ont.). Serum separator tubes were from Becton Dickinson (Rutherford, N.J.), and horseradish peroxidase (HRP)-conjugated goat anti-mouse IgG+IgM from Caltag (South San Francisco, Calif.).

Bacterial Lipids

Total lipids were extracted from frozen cell pastes of different species of archaeobacteria, and the total polar lipids (TPL) were collected as the acetone insoluble fraction as described (20). When required, lipids in biologically pure form were obtained from the mixture of extracted lipids by using preparative thin layer chromatography, and purity was confirmed by negative-ion fast atom bombardment mass spectrometry. PGP-Me (2,3-diphytanyl-sn-glycerol-1-phospho-3'-sn-glycerol-1'-methylphosphate) was purified from *Halobacterium cutirubrum* (9); $D_{OH}PI$ (hydroxydiether analog of phosphatidylinositol) and $D_{OH}PG$ (hydroxydiether analog of phosphatidylglycerol) were purified from *M. mazei* (19); and a phosphatidylinositol glycotetraether lipid of m/z 1703 daltons was purified from lipids extracted from *M. smithii*. It will be recognized by one skilled, that the lipids may be extracted and/or purified by methods other than those described here, to obtain acceptable lipids for the utility described.

Liposome and Archaeosome Preparation

For liposome and archaeosome preparation, the lipids dissolved in chloroform were dried under a stream of $N_2$, and placed in a lyophilizer for 1–2 hours prior to hydration. Hydration buffer consisted of 0.5 ml of 10 mM potassium phosphate buffer, pH 7.14, containing 160 mM NaCl (PBS). Unless indicated otherwise, liposomes and archaeosomes were made by pressure extrusion of the hydrated lipids through two stacked 400 nm filters in a LiposoFast apparatus similar to that described by MacDonald et al. (10) to obtain predominantly unilamellar vesicles. Archaeobacterial lipids were hydrated for 1–2 hours, or sometimes overnight, at 35° C. and the resulting multilamellar vesicles were either used directly (when specified) or extruded at ambient temperature. Conventional phospholipids were hydrated (1–2 h) and extruded at 50° C. for DPPC, and at 35° C. for DMPC:D-MPG:cholesterol (1.8:0.2:1.5, molar ratio) or DMPC:D-MPG (1.8:0.2, molar ratio) to obtain unilamellar vesicles.

Vesicles with entrapped CF or peroxidase were prepared for in vitro phagocytosis studies, by incorporating into the hydration buffer 1.5 mM CF or 100 μg peroxidase (138 units), respectively. Typically, 10 mg of dried TPL extracted from the specified archaeobacterium, or either of the conventional lipids DPPC or DMPC:DMPG:CHOL at the molar ratio indicated above, were hydrated for vesicle formation by pressure extrusion, as described above. Unencapsulated CF in CF-vesicle preparations was removed in Sephadex G-50 columns using the minicolumn centrifugation method described by New (14). In the case of peroxidase-vesicles, unbound enzyme was removed by centrifugation (200,000× g, max, 30 min) and the vesicles washed 4–5 times with 7 ml aliquots of PBS.

The in vitro uptake of archaeosomes prepared from the TPL extracted from *M. mazei* and of conventional liposomes prepared from DPPC:CHOL (5:5 molar ratio), DSPC:CHOL (5:5 molar ratio) or DSPC:CHOL:DCP (4:5:1 molar ratio) was also studied using cholesteryl [1-$^3$H] hexadecyl ether ($^3$H-chol) as the lipidic marker. $^3$H-chol dissolved in chloroform, was added (1 μCi/mg total lipid) to the respective lipid mixture before drying the lipids. When required, coenzyme $Q_{10}$ dissolved in chloroform was added (at 5:20 weight/weight ratio of total lipids) before drying the lipids. The liposomes and archaeosomes were prepared by the reverse-phase evaporation (REV) method (at 55° C. ) combined with bath sonication (at room temperature), using the method as described by New (13). $^3$H-chol incorporation into these vesicles was at an efficiency of at least 95%, and these vesicles had essentially the same specific activities. Material unassociated with the vesicles was removed by centrifugation and washing with PBS as described above.

For in vivo tissue distribution studies, the various vesicles with $^3$H-chol as the lipidic marker, were prepared as described below. When indicated, these vesicles also contained coenzyme $Q_{10}$ and/or distearoylphosphatidylethanolamine-polyethylene glycol 5000 conjugate (DSPE-PEG), which were added to the rest of the lipids before drying. Archaeosomes (*M. mazei* TPL), $CoQ_{10}$-archaeosomes (*M. mazei* TPL:$CoQ_{10}$ at a molar ratio of 8:2 using the average molecular weight of the TPL as 1000), PEG-archaeosomes (*M. mazei* TPL plus DSPE-PEG at 7% molar ratio of the total lipids), and PEG-$CoQ_{10}$-archaeosomes (*M.mazei* TPL:$CoQ_{10}$ at a molar ratio of 8:2 plus DSPE-PEG at 7% molar ratio of the total lipids) were prepared with $^3$H-chol (specific activity of 52 μCi/mmole) added at 10 μCi per mg of total lipid used for vesicle preparation. Vesicles were prepared by the REV-bath sonication method described above for preparing $^3$H-chol-labeled vesicles for in vitro studies.

Conventional liposomes (DSPC:DCP:CHOL at a molar ratio of 4:1:5), $CoQ_{10}$-conventional liposomes (DSPC:DCP:CHOL:$CoQ_{10}$ at a molar ratio of 3:1:4:2), PEG-conventional liposomes (DSPC:DCP:CHOL at a molar ratio of 4:1:5 plus DSPE-PEG at 7% molar ratio of the total lipids), and PEG-$CoQ_{10}$-conventional liposomes (DSPC:DCP:CHOL:$CoQ_{10}$ at a molar ratio of 3:1:4:2 plus DSPE-PEG at 7% molar ratio of the total lipids) were prepared with $^3$H-chol as described above for archaeosomes.

For in vivo studies with archaeosomes (prepared from the TPL, or a lipid obtained in a biologically pure form from the indicated archaeobacterium) and conventional liposomes (prepared from DMPC:DMPG at 1.8:0.2 molar ratio, or DMPC:DMPG:CHOL at 1.8:0.2:1.5 molar ratio, or DMPC:DCP:CHOL at 7:1:2 molar ratio) containing entrapped antigen, the vesicles were prepared by pressure extrusion (at room temperature for archaeobacterial and at 35° C. for DMPC-containing lipids, using 400 nm pore size filters). About 20 mg dry weight of the dried lipid(s) was hydrated in 1 ml PBS containing either BSA (5 mg/ml), Cholera B toxin subunit (0.5 mg/ml), or O-chain polysaccharide (18 mg/ml). To entrap BSA in DSPC:DCP:CHOL (4:1:5, molar ratio), in DSPC:DCP:CHOL:$CoQ_{10}$ (3:1:4:2, molar ratio), and *M. mazei* TPL:$CoQ_{10}$ (8:2, molar ratio), the vesicles were prepared by the REV (at 55° C.)-sonication method described above. The BSA was encapsulated in these vesicles by the DRV method as described by New (13). The antigen that was not entrapped/associated with the vesicles was removed by centrifugation and washing as described for peroxidase-vesicles.

Vitamin E was incorporated into archaeosomes by dissolving in $CHCl_3$, 1 mg vitamin E and 20 mg of *T. acidophilum* TPL. The $CHCl_3$ was removed, the dried lipids and vitamin E hydrated with PBS, and vitamin E-archaeosomes prepared by pressure extrusion, as described above.

It will be understood by one skilled in the art that the preparation of liposomes and archaeosomes of this invention and the association/incorporation of other compounds in the respective vesicles is not limited to the illustrated methods, and may also be made using other methods of record in the published literature. The vesicles of this invention may also be prepared and used in conjunction with additional compounds known to have beneficial properties, such as serving as an additional adjuvant.

Vesicle Characterization

The mean vesicle diameters were determined by number-weighted size distribution using a Nicomp particle sizer, model 370 (Nicomp, Santa Barbara, Calif.).

Peroxidase activity in 5 to 35 μg dry weight of liposomes or archaeosomes was assayed in 1 ml reaction mixtures containing 45 mM citric acid, pH 4.0, 2.2 mM $H_2O_2$, 0.2 mM 2,2'azino-bis (3-ethylbenzthiazoline-6-sulfonic acid), in the presence of 0.5% (w/v) of the detergent OGP. Reaction rates were recorded at 23° C. with a Coleman 575 recording spectrophotometer.

CF was quantitated with a spectrofluorometer set at an excitation wavelength of 470 nm and an emission wavelength of 520 nm.

The amount of protein incorporated into or associated with archaeosomes and liposomes to be used for immunizations was quantitated by SDS polyacrylamide gel electrophoresis (PAGE), wherein the lipids separate from the protein antigen. Densitometry of stained gels was done with a gel documentation system from Canberra Packard Canada, and quantitated from standard curves prepared by loading 0.025 to 2 μg of the protein of interest onto each lane. The amount of protein incorporated/associated with the vesicles was compared on the basis of salt free dry weights of the liposomes or archaeosomes, respectively.

To determine the amount of coenzyme $Q_{10}$ entrapped in the lipid layer of vesicles, the vesicles were dissolved in chloroform and the absorbency was measured at 278 nm. A standard curve was prepared using purified $Q_{10}$ dissolved in chloroform, and a concentration of 10 μg $CoQ_{10}$/ml gave an absorbency of 0.2.

Murine Peritoneal Macrophages and Cell Lines

Murine peritoneal macrophages, harvested from 12–16 week old female Balb/c mice as previously described (23), were maintained in RPMI-1640 medium supplemented with 25 mM HEPES buffer, 2 mM L-glutamine, 40 μg/ml gentamicin, and 10% FBS. HEp-2 (human laryngeal epithelial carcinoma cell line, ATCC #CCL 23), and HeLa (human cervical epitheliod carcinoma cell line, ATTC #CCL 2), and the monocyte-macrophage cell line J774A.1 (ATCC #TIB 67) were obtained from the American Type Culture Collection, Rockville, Md. These three cell lines were maintained in the same medium as were the peritoneal macrophages. EJ/128 cells (human uroepithelial carcinoma cell line) were obtained from Dr. Derek Duke, Imperial Cancer Research Fund, London, England. EJ/128 cells were maintained in DMEM supplemented with 2 mM L-glutamine, 40 μg/ml gentamycin and 10% FBS. All cells were sustained at 37° C. in a humidified atmosphere containing 5% $CO_2$ in air.

Peroxidase Assay for in vitro Vesicle Binding to Cells

Archaeosomes or liposomes containing encapsulated peroxidase were incubated with different cell types to quantitate the respective vesicle binding to mammalian cells. Peritoneal macrophages were prepared as described previously to give confluent monolayers (23). The cell lines were seeded at 50% of confluence onto tissue culture plates (Nunc Inc., Naperville, Ill.). All the cell lines, in their respective media, were plated onto 96-well tissue culture plates to form confluent monolayers. The next day, the cells were washed twice with the respective growth medium to remove non-adherent cells and then incubated (50 min at 37° C.) in fresh medium supplemented with the various vesicle preparations. The adherent cells were then washed 5× with 200 µl ice-cold PBS containing 0.9 mM $CaCl_2$, to remove unbound vesicles. The vesicles and cells were subsequently lysed using 100 µl of 0.5% OGP, and 100 µl of 2× concentrated substrate solution was added. After 30 min incubation at 25° C., the colour reaction was measured at 405 nm using a Dynatech MR5000 microplate reader (Chantillym, Va.). The readings were converted to µg of vesicles bound per mg of cell protein, based on the amount of peroxidase that was encapsulated in the respective vesicles used in the binding assay.

Fluorescence Microscopy Assessment of in vitro Vesicle Binding to Cells

Fluorescence microscopy was performed to visualize archaeosome or liposome binding to several cell types. For these studies, CF was entrapped within the vesicles at a concentration of only 1.5 mM, to avoid self-quenching. Peritoneal macrophages and the various cell lines were seeded at approximately 20% of confluence onto 24-well tissue culture plates (Nunc Inc., Naperville, Ill.). The next day the cells were washed twice with ice-cold PBS containing 0.9 mM $CaCl_2$ to remove non-adherent cells and incubated with the various CF-containing vesicle preparations (40 µg/ml) for 30 min at 37° C. The cells were washed extensively with ice-cold PBS and then preserved in PBS containing 1% formaldehyde and 0.1% n-propylgallate (fluorescence fading inhibitor). The adherent cells and bound CF-vesicles were observed using an Olympus IMT-2 inverted microscope fitted with an IMT2-RFL reflected light fluorescence attachment and a 35 mm photomicrographic camera.

$^3$H-chol Assay for in vitro Vesicle Uptake

These uptake studies were performed essentially as described above, but used liposomes and archaeosomes prepared to contain tritiated cholesteryl [1-$^3$H] ether ($^3$H-chol) as a tracer. One micro curie (1 µCi=37 kBq) of $^3$H-chol was added per milligram of lipid before making the vesicles. Radioactive label taken up by J774A.1 macrophages was assayed and calculated on the basis of the amount of macrophage protein, according to Makabi-Panzu et al. (11).

Inhibition of Macrophage Functions

Adherent macrophages were treated to inhibit their phagocytic functions, and the influence of this on archaeosome binding/uptake was monitored. J774A.1 macrophages were seeded in 24-well tissue culture plates to form semi-confluent monolayers. The next day the cells were washed twice with ice-cold PBS. CF-containing archaeosomes prepared from the TPL of M. hungatei were added to the macrophages at a concentration of 0.04 mg/ml and the samples were allowed to incubate for 30 min at 37° C. The cells were then washed extensively with ice-cold PBS containing 0.9 mM $CaCl_2$ to remove non-adherent archaeosomes and the cells were resuspended in fresh media alone, in media containing inhibitors, or in media cooled to 4° C. The cultures were then incubated for up to 300 min at 37° C. (or 4° C., as indicated). At required time intervals, macrophages were examined by fluorescence microscopy to obtain an estimate of the extent of CF release from the archaeosomes.

For assays using formaldehyde-fixed macrophages, the cells were first incubated with archaeosomes and washed as described above. Then, 0.5 ml of a 0.5% formaldehyde solution was added to each well and the cells were incubated at room temperature for 15 min. The fixative was removed by extensive washing with PBS and media, prior to the start of incubation for up to 240 min.

To examine the effects of inhibition of the polymerization of cytoskeletal components of the cells on archaeosome uptake, macrophages were incubated in media containing 10 µg/ml each, of cytochalasins B and D (in a final concentration of 1% dimethyl sulfoxide) beginning 30 min prior to the addition of archaeosomes, and continuing to the end of the time trial period. Macrophages were also incubated under the same conditions in media containing 1% dimethyl sulfoxide (DMSO) to evaluate any possible effect of DMSO.

In vivo Tissue Distribution of Vesicles

Inbred female Balb/c mice were purchased from Charles River Laboratories (St. Constant, Quebec) and maintained in the Animal Care Unit at the National Research Council of Canada.

Various types of vesicles containing $^3$H-chol were administered to Balb/c female mice (1 mg total lipids per mouse, ca. 50 mg/Kg of body weight), in triplicate, via the p.o. route using -intra gastric intubation to deliver directly to the stomach, via the i.m. route, via the s.c. route, or via the i.v. route (injected in the tail vein). The mice were 6–8 weeks old at the time of vesicle administration. The mice were allowed normal access to food and water. After 24 or 48 hours post-administration, the mice were euthanised, plasma and organs were collected, and the radiotracer counts associated with the organ tissues were determined in an LKB 1217 Rackbeta liquid scintillation counter (Pharmacia Canada, Baie d'Urfé, Que.) using methods described previously (12). The distribution of the radiotracer per gram of the various organ tissues (or per ml plasma) was calculated and expressed as a percentage of the total radiotracer count administered to the animal at time zero (% dose/g tissue).

Immunization Protocols

The immunization strategies were similar for each of the different experiments. For each experiment, details of the amounts and types of antigen/adjuvant injected, and the time intervals between injections is described in the appropriate figure legends. Freund's adjuvant (FA) encompasses Freund's complete adjuvant (CFA) and Freund's incomplete adjuvant (IFA) used at 62.5% strength in PBS. For each antigen/adjuvant preparation three mice were injected (unless indicated otherwise) i.p., i.m., or s.c. with antigens encapsulated in archaeosomes or liposomes (diluted in sterile PBS, pH 7.1), antigens emulsified in CFA, or with antigens diluted in PBS alone (final volume, 0.2 ml/mouse). For the second immunization, mice were injected with antigens encapsulated in archaeosomes or liposomes, or emulsified in IFA, or diluted in PBS. For experiments where a third or fourth injection was required, antigens were injected either encapsulated in the respective vesicle type or as bare antigen diluted in PBS. Mice were 6–8 weeks of age at the time of the first immunization.

Mice were bled from the tail veins usually four days after each injection. The blood was allowed to dot, and cells removed from the serum by centrifuging in serum separator tubes.

In vivo Administration

Administration of the vesicles which carry the antigen, drug or other ingredients is by the customary routes, and may be used with additional substances, such as carbonate buffer when given orally. The required dose of antigen will vary depending on the antigen used and on the route of administration, but is about 1 to 50 µg per dose. Entrapments of protein antigens in the vesicles range from about 0.9–208 µg/mg dry weight of vesicles, or 0-chain polysaccharide up to 500 µg/mg vesicles. Coenzyme $Q_{10}$ may be incorporated from 0 up to about 0.23 mg/mg vesicles, and vitamin E from 0 up to about 0.2 mg/mg vesicles with 0.05 mg/mg preferred. Generally, the dosage of vesicles is in the range of 4 to 73 mg/kg body weight, based on a weight of 25 g/mouse.

Nevertheless, it may be necessary, under certain circumstances, to deviate from the amounts mentioned, and in particular to do so as a function of the body weight or of the nature of the administration method, the nature of its formulation, the animal species, and the time or interval over which the administration takes place. Thus, it can in some cases be sufficient to manage with less than the above-mentioned amount, whereas in other cases more than the upper limit mentioned may be required.

Enzyme-linked Immunosorbent Assays

The humoral response was measured by the indirect enzyme-linked immunosorbent assay (ELISA) using a variety of solid-phase adsorbed antigens. BSA, Cholera B toxin subunit, or E. coli 0:157:H7 lipopolysaccharide was diluted in distilled water (15 µg/ml final concentration) and 100 µl/well was dried (overnight incubation at 37° C.) to coat the ELISA microplate wells. All indirect ELISA assays were performed using standard methods. Dilutions of antibody-containing sera were used as the first antibody and a 1/1500 dilution of HRP-conjugated goat anti-mouse IgG+IgM as the detection antibody.

The isotypes of anti-BSA antibodies raised in mouse sera were assayed by an ELISA method. Wells were coated with BSA (as above). Dilutions of each serum were titred with peroxidase-coupled sheep anti-mouse IgG1, IgG2a, IgG2b, IgG3, and IgM. All ELISA data are reported as the means ± sample standard deviations.

Results and Discussion

Construction and Characterization of Archaeosomes and Liposomes

Peroxidase encapsulated within vesicles was used to quantitate the relative uptake of the various types of archaeosomes and of conventional liposomes, by eukaryotic cells. The amounts of each vesicle type taken up by adherent cells seeded onto culture wells could be quantitated by measuring peroxidase activity following lysis/permeabilization of both cells and associated vesicles by detergent.

Archaeosomes were prepared from the TPL extracted from several archaeobacteria, and conventional liposomes prepared from two conventional phospholipid formulations that have been frequently used in the prior art (2, 17). The percentage of the total peroxidase which was exposed on the vesicle surface could be estimated by comparing the rate of the enzyme reaction in whole vesicles and in OGP-permeabilized vesicles (Table 1).

Figure 2:
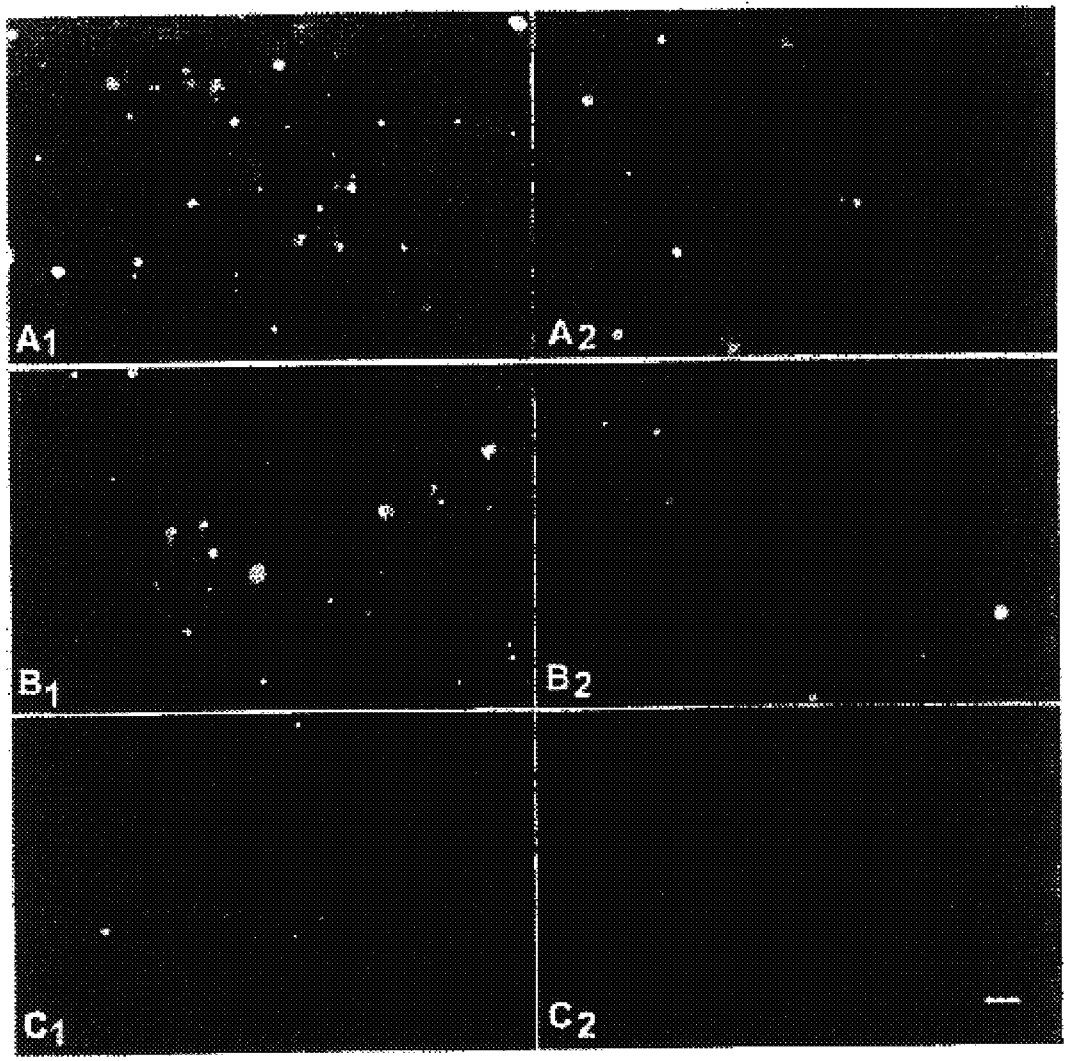
FIG. 2. Fluorescence micrographs of murine peritoneal macrophages, J774A.1, and HEp-2 cells incubated with multilamellar *M. mazei* archaeosomes ($A_1$, $B_1$, $C_1$), or multilamellar conventional liposomes prepared from DMPC:DMPG:CHOL ($A_2$, $B_2$, $C_2$), each vesicle type containing CF. Panels $A_{1-2}$, J774A.1 cells. Panels $B_{1-2}$, murine peritoneal macrophages. Panels $C_{1-2}$, HEp-2 cells. Yellow-fluorescence of vesicles appears in the black and white photos as light areas. Magnification bar=20 µm.

Except for the data in FIG. 2, we prepared intermediate-sized vesicles of approximately 200 nm diameter by pressure extrusion of hydrated multilamellar liposomes through filters of 400 nm pore size. This resulted in populations of vesicles with the size range distributions defined in Table 1. The distributions were quite narrow except for DPPC liposomes, which consisted of two differently sized populations.

Binding of Archaeosomes and Conventional Liposomes to Cells

Binding and uptake of the immunogen by macrophages or other antigen processing/presenting cells is the basis for the induction of an immune response. Peroxidase and fluorescence assays were used to quantitate and compare the binding of several types of archaeosomes and of conventional liposomes to two phagocytic and three non phagocytic cell lines. The results are illustrated in FIG. 1, and in Tables 2 and 3. The uptake of archaeosomes by the two macrophage lines (murine peritoneal and J774A.1 macrophages) was several times greater than the conventional liposomes. Compared with macrophage cell lines, the uptake of archaeosomes and of conventional liposomes by non-phagocytic cell lines (Hep-2, HeLa, EJ/28) was substantially lower.

Large, multilamellar vesicles (0.5 to 3 µm) prepared from the polar lipids of M. mazei or from DMPC:DMPG:cholesterol gave trends similar to those obtained with the smaller vesicles, i.e. greater uptake of archaeosomes than conventional liposomes by murine peritoneal macrophages, and by J774A.1 cells; lesser uptake of both vesicle types by the non-phagocytic HEp-2 cell line (FIG. 2).

These data, using encapsulated peroxidase or fluorescent dye as markers, illustrate the enhanced phagocytosis of archaeosomes compared with conventional liposomes. The potential advantages for using archaeosomes for delivery of compounds to macrophages is discussed elsewhere in this submission.

Effect of Inhibition of Macrophage Functions on Archaeosome Binding

To determine if archaeosome populations were actively phagocytosed, as opposed to adhered to the surface, macrophages were treated with inhibitors of phagocytosis (Table 4). As demonstrated by the control population of untreated macrophages exposed to archaeosomes, the amount of fluorescence associated with these macrophages was seen to decrease markedly over time. This is consistent with internalization of the archaeosomes, followed by release of the encapsulated dye due to degradation of the vesicle. In contrast, treatments which are typically known to inhibit membrane flow and thus phagocytosis, such as decreased temperature, the addition of cytochalasins, or fixation with formalin, resulted in little or no decline in the fluorescence (present due to initial binding of vesicles, before inhibition of phagocytosis) of the macrophages over the time periods studied. This indicates that the inhibitors prevented internalization of the liposomes into the macrophages. In addition, the time-dependent decline in fluorescence upon readjustment of the temperature of the culture medium from 4° C. back to 37° C. demonstrated that the macrophages recovered their phagocytic abilities. An appropriate model encompasses an initial binding to the cell surface, followed by phagocytosis, and degradation of the internalized vesicles.

Use of Coenzyme $Q_{10}$ to Enhance the Uptake of Vesicles by Cell Lines

Coenzyme $Q_{10}$ was entrapped into archaeosomes prepared from the TPL of M. mazei, which are known to be anionic (19), and into anionic conventional liposomes (DSPC:CHOL:DCP), with relatively high entrapment efficiencies (Table 5). However, compared with anionic lipid mixtures, even higher entrapment efficiencies were obtained with vesicles prepared with neutral lipid mixtures DPPC-:CHOL and DSPC:CHOL. The loading ratios shown are representative of those used in subsequent experiments (Tables 6–7).

The uptake by macrophages, of archaeosomes and of conventional liposomes lacking coenzyme $Q_{10}$ is shown as a function of time using $^3$H-chol as the tracer marker (Table 6A). At 37° C., at the indicated times, it can be seen that M. mazei archaeosomes are taken up substantially better than all formulations of conventional liposomes, as was also shown in Table 2. The data in Table 6A serve as control values to assess the effect on vesicle uptake of incorporating coenzyme $Q_{10}$ into the vesicles (Table 6B). These data show that the cellular accumulation of all vesicle types, by the macrophages, was markedly enhanced when the vesicles contained coenzyme $Q_{10}$. This enhancing effect of coenzyme $Q_{10}$ was several times higher with the archaeosomes than with the conventional liposomes. Comparable profiles of accumulation and the enhancing effects of coenzyme $Q_{10}$ entrapment on the uptake of archaeosomes and of conventional liposomes, was observed at all lipid concentrations tested (compare Tables 7A and 7B).

These results clearly indicate the potential for inclusion of coenzyme $Q_{10}$ into the vesicles for increased targeting of archaeosomes and of conventional liposomes to various cell types. An increased uptake of vesicles containing coenzyme $Q_{10}$ by macrophages (antigen processing cells, and the sites for some infectious agents) dearly indicates application in delivery of antigens, and drugs (including antiviral and antimicrobial agents). Another application is to deliver the water-insoluble drug (coenzyme $Q_{10}$) to mammalian cells, via liposomes and archaeosomes.

Archaeosomes prepared from vitamin E and the TPL of *T. acidophilum*, as an example, could be made. Incorporation of 1 mg vitamin E into 20 mg lipids resulted in archaeosomes with the expected size range of 220±88 nm following extrusion through 400 nm pore size membranes.

In vivo Tissue Distribution of Vesicles

The distribution, into various tissues, of the $^3$H-chol lipidic radiotracer marker incorporated into the vesicle layer was used to predict the delivery of the vesicles and/or the associated/encapsulated compounds to the specific organ tissues. Cholesteryl [1-$^3$H] ether is a non-metabolized radiotracer (marker) suitable for studying tissue distribution of lipidic vesicles in animals such as mammals (15).

Figure 3:
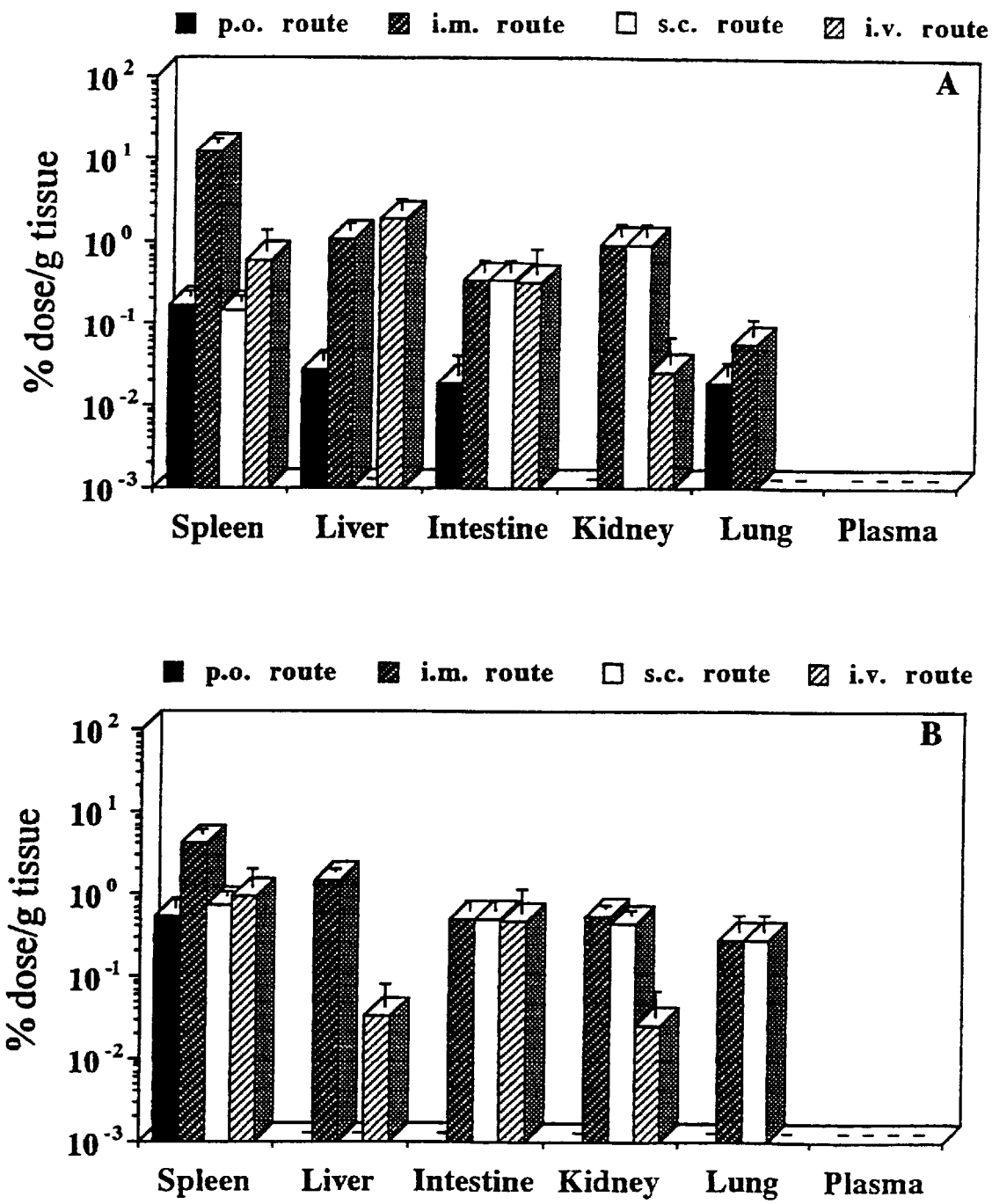
FIG. 3. Tissue distribution of (A) conventional liposomes (DSPC:DCP:CHOL) and, (B) $CoQ_{10}$-conventional liposomes (DSPC:DCP:CHOL:$Q_{10}$) 24 hours after oral and parenteral administration to mice. The data shown are ± sample standard error from the mean.

The tissue distribution profiles of label from conventional liposomes and $CoQ_{10}$-conventional liposomes administered by various routes showed that these were generally similar (FIGS. 3A and 3B). However, the major difference was that in orally administered $CoQ_{10}$-conventional liposomes, no accumulation of the label (at 24 h) was seen in any of the tissues examined, except for in the spleen.

PEG conjugated to lipids, such as DSPE, has been used in conjunction with conventional lipids to prepare vesicles with altered surface properties, to evade capture by the cells of the reticuloendothelial system (predominantly present in the spleen and liver), and hence prolong the circulation half life in the blood. Such liposomes have been called sterically stabilized liposomes (24). The tissue distribution profile of PEG-conventional liposomes (FIG. 4A) was somewhat similar to that of conventional liposomes (FIG. 3A). However, A was surprising to see that when $CoQ_{10}$ was incorporated into the PEG-conventional liposomes which were administered orally, there was an increased accumulation of the marker (24 hours post administration) into spleen, liver, intestine, kidney and lung tissues (FIG. 48). The combined accumulation in the spleen and liver was about 8-fold greater. With the i.v. route of administration, the PEG-$CoQ_{10}$-conventional liposomes showed no presence of the marker in the spleen (FIG. 4B).

Figure 5:
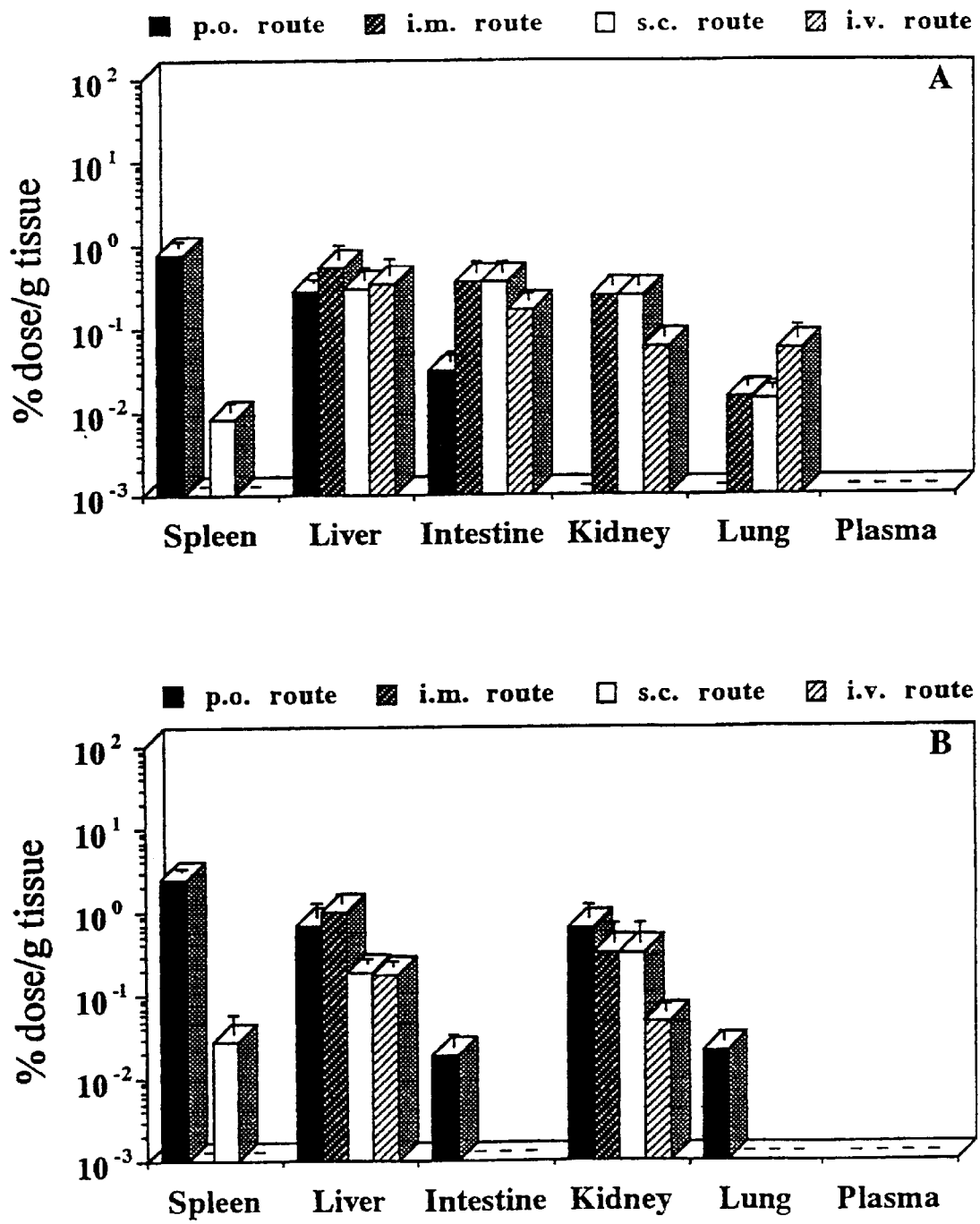
FIG. 5. Tissue distribution of (A) archaeosomes (*M. mazei* TPL) and, (B) $CoQ_{10}$-archaeosomes (*M.mazei* TPL:$Q_{10}$) 24 hours after oral and parenteral administration to mice. The data shown are ± sample standard error from the mean.

Except for the accumulation in the intestine and kidneys, the tissue distribution profiles of *M. mazei* archaeosomes (FIG. 5A) showed differences from those with conventional liposomes (FIG. 3A). When *M. mazei* archaeosomes were administered via i.m., s.c., or i.v. routes, the tissue distribution profile (at 24 h), with and without $CoQ_{10}$ entrapped in the vesicles, was similar except for that in the intestines (FIGS. 5A and 5B).

Figure 6:
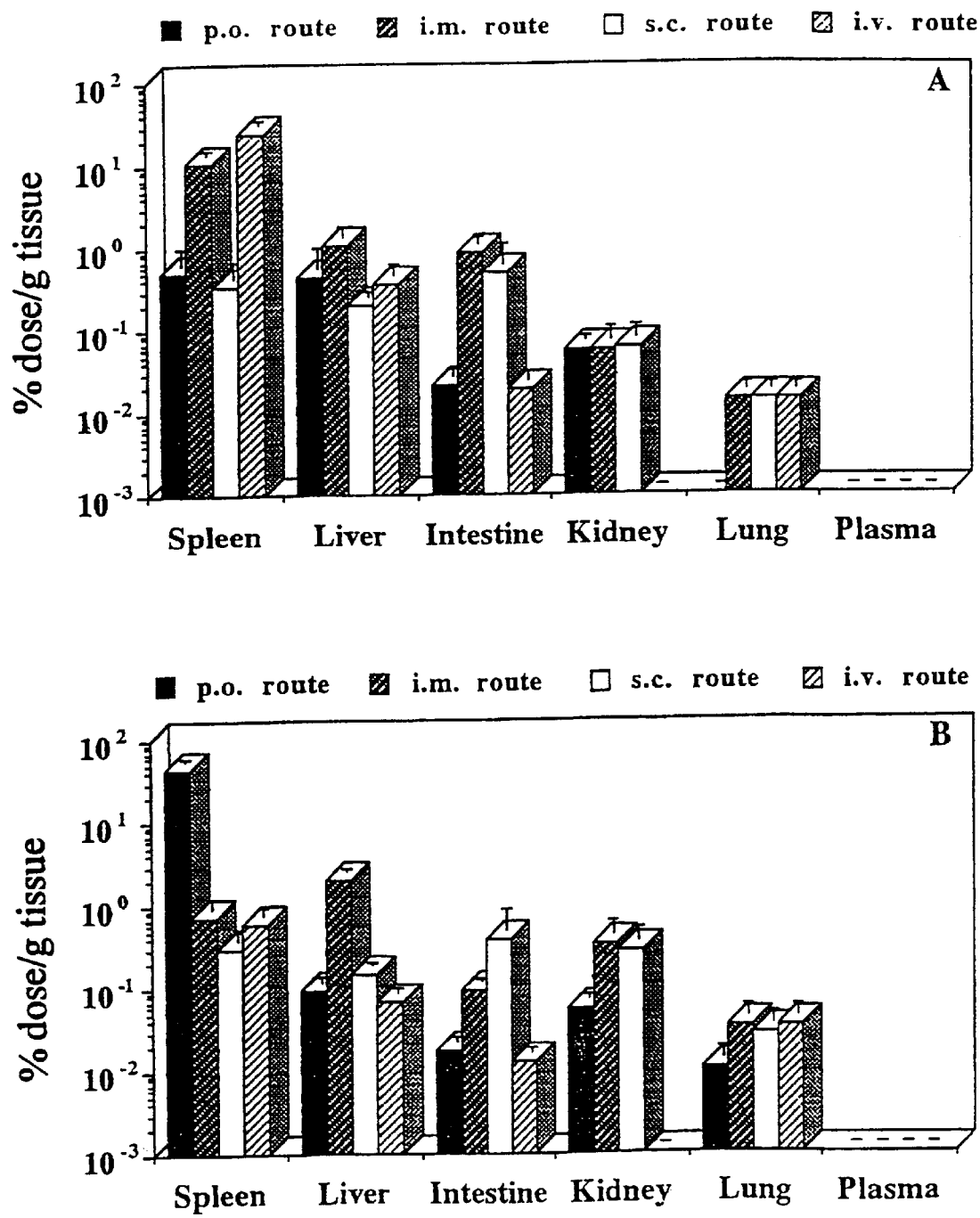
FIG. 6. Tissue distribution of (A) PEG-archaeosomes (*M.mazei* TPL:DSPE-PEG) and, (B) PEG-$CoQ_{10}$-archaeosomes (*M.mazei* TPL:DSPE-PEG:$Q_{10}$) 24 hours after oral and parenteral administration to mice. The data shown are ± sample standard error from the mean.

It was very surprising to see that in the case of orally administered PEG-$CoQ_{10}$-archaeosomes, the accumulation of the label (24 h post-administration) in the spleen was up to 80-fold higher than that seen with PEG-archaeosomes (FIGS. 6A and 6B). This accumulation in the spleen represented about 40% of the total administered label. The combined level of incorporation of orally delivered PEG-$CoQ_{10}$-archaeosomes in the liver and spleen, was about 5-fold better than the highest level obtained (FIG. 4B) with any combination using conventional liposomes. For i.m. and i.v. administered PEG-$CoQ_{10}$-archaeosomes, the accumulation of label in the spleen was significantly lower than that obtained in the absence of $CoQ_{10}$ (i.e., in PEG-archaeosomes).

Figure 4:
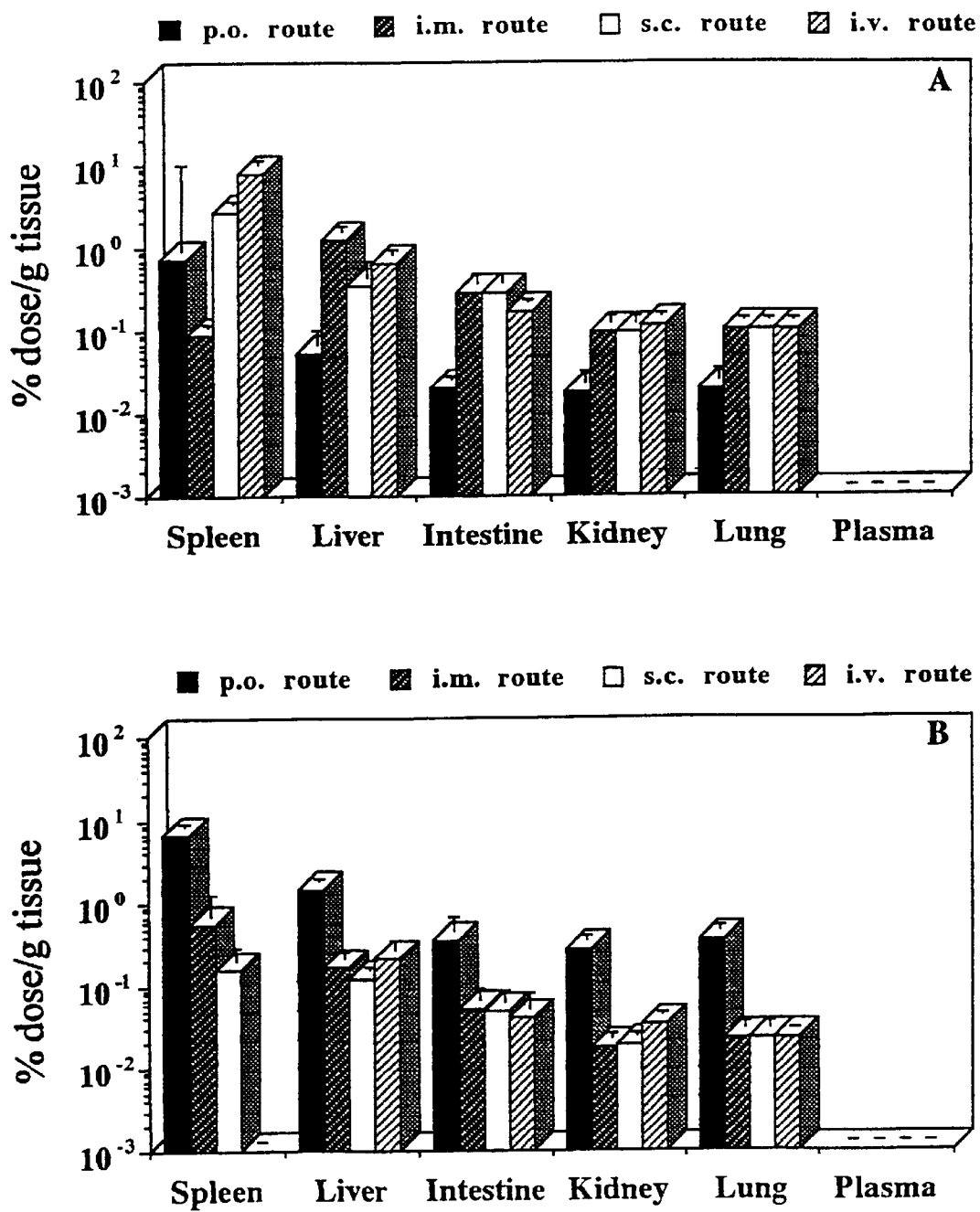
FIG. 4. Tissue distribution of (A) PEG-conventional liposomes (DSPC:DCP:CHOL:DSPE-PEG) and, (B) PEG-$CoQ_{10}$-conventional liposomes (DSPC:DCP:CHOL:DSPE-PEG:$Q_{10}$) 24 hours after oral and parenteral administration to mice. The data shown are ± sample standard error from the mean.

The 48 hour tissue distribution profile of label from orally administered PEG-$CoQ_{10}$ conventional liposomes was similar to that observed at 24 hours (FIG. 4B). However, the 48 hour tissue distribution profile of label from orally administered $CoQ_0$-archaeosomes, whether or not also associated with PEG, indicated that the amount in spleen, liver and intestines had declined to about 0.001%, each, of the administered dose, from the respective higher levels (FIGS. 5B and 6B) at 24 hours. At 24 hour post-administration there was no detectable label in the serum, irrespective of the vesicle type or the route of vesicle administration (FIGS. 3–6).

The data in these figures show that a significant enhancement in the efficacy of the delivery/accumulation of orally administered conventional liposomes, to the spleen and liver (the major sites for the antigen processing cells of the immune system), can be achieved by incorporation of $CoQ_{10}$ in these vesicles. The delivery to the spleen and liver by orally administered vesicles can be further enhanced dramatically, by using PEG-$CoQ_{10}$-archaeosomes. It is also evident that by using different combinations of vesicle types, with and without entrapped $CoQ_{10}$, one can obtain various different tissue distribution profiles. This offers a means to alter the tissue targeting for different applications in the fields of medicine.

Immune Responses

The enhanced uptake of archaeosomes by phagocytic cells, compared to that of conventional liposomes, suggested that archaeosomes may be superior as adjuvants and/or carriers of antigens for raising an immune response to an immunogen. This was found to be the case in animal model studies using mice.

Figure 7:
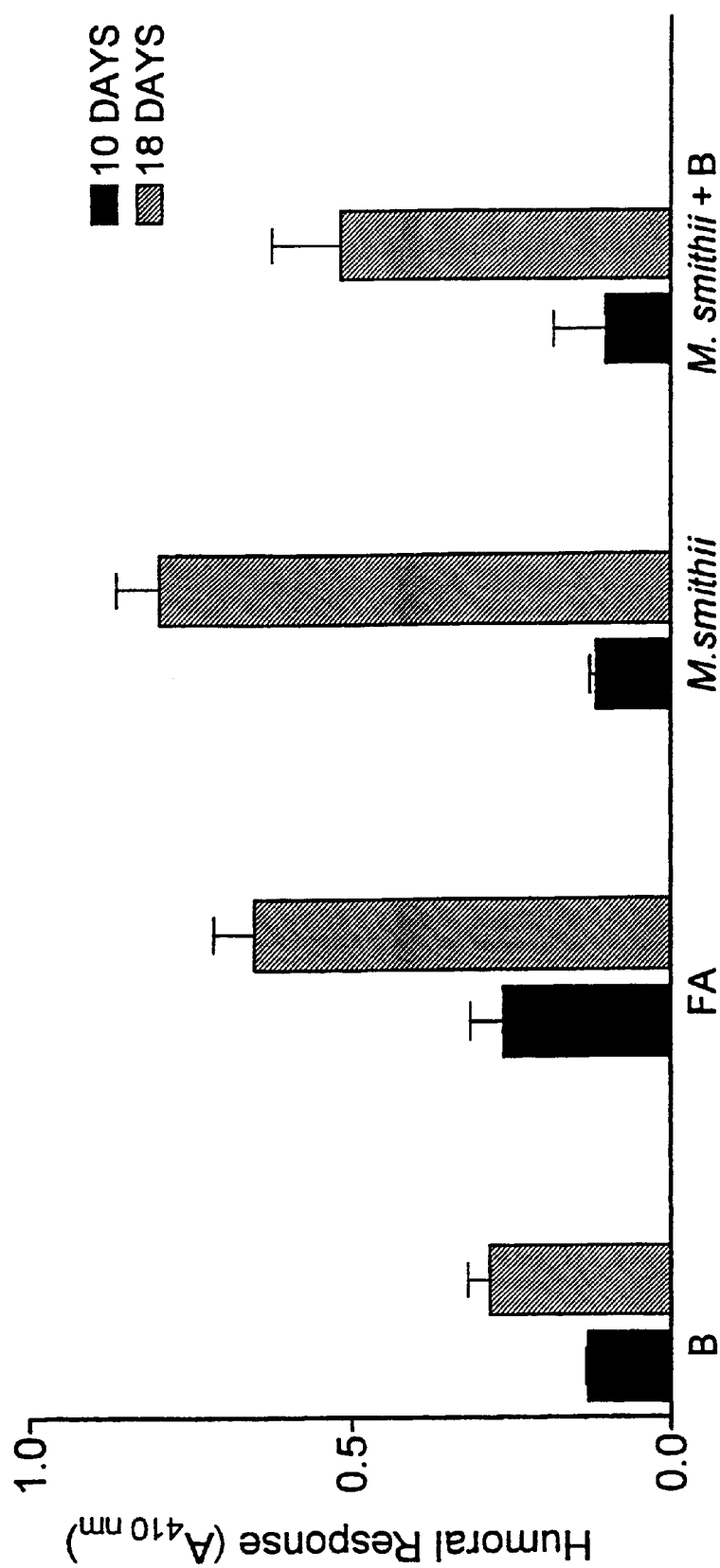
FIG. 7. Murine humoral responses to Cholera B subunit as antigen. First and second injections (i.p.) consisted of: B, 1.0 µg of antigen in PBS (no adjuvant), FA, 1.0 µg of antigen+Freund's adjuvant; *M. smithii*, archaeosomes (1.21 mg lipid, 1.0 µg antigen encapsulated); and *M. smithii*+B, bare archaeosomes (1.21 mg lipid) followed 1 hour later by 1.0 µg of antigen in PBS. Immunizations were at days 0 and 14.

Compared to control mice receiving the bare antigen, the antibody titer in sera from mice immunized with cholera toxin B subunit was found to be significantly higher when the antigen was entrapped in archaeosomes of *M. smithii*, and this response was even comparable to that observed with Freund's adjuvant (FIG. 7).

Figure 8:
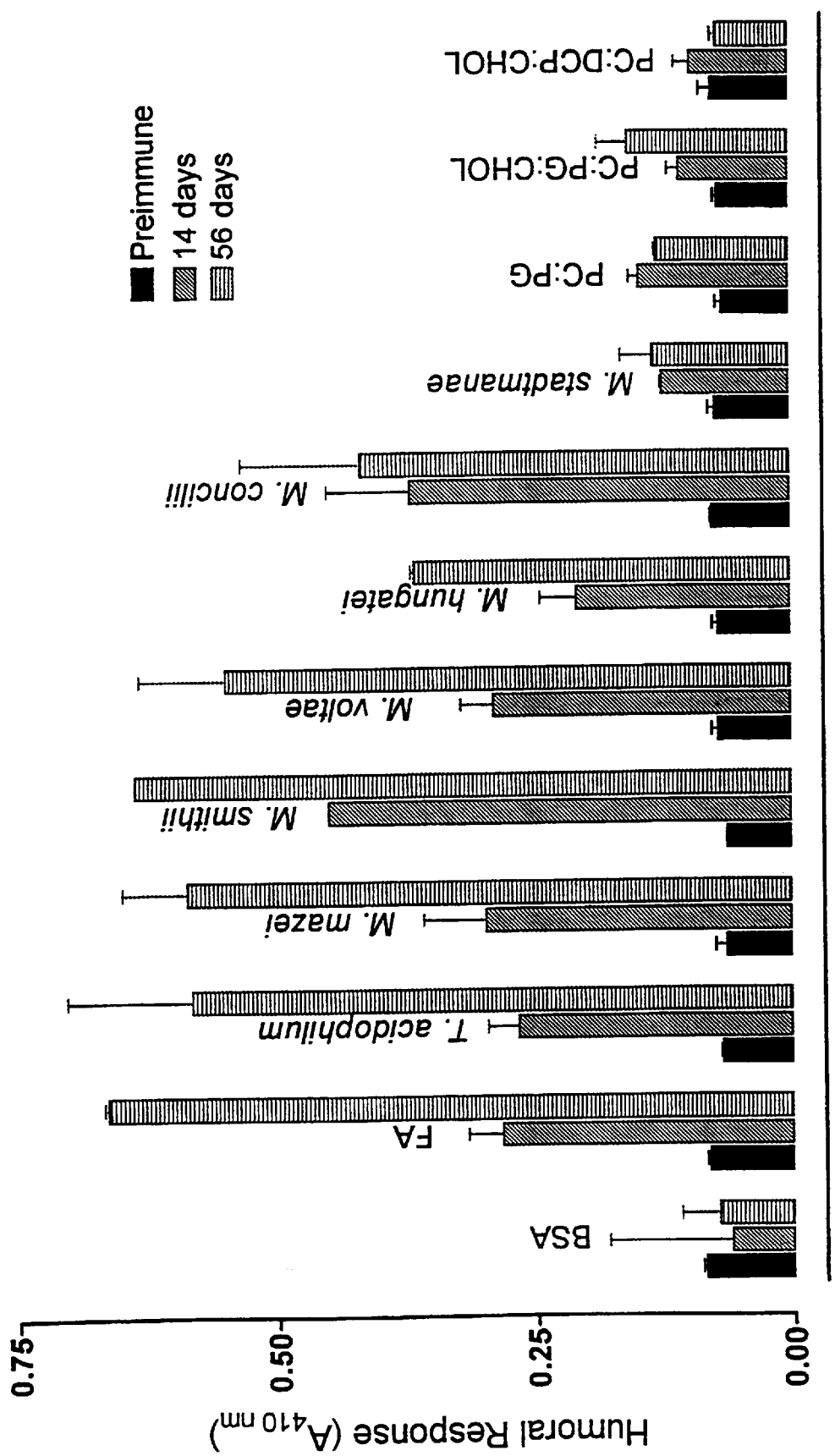
FIG. 8. Comparison of murine humoral responses to bovine serum albumin (BSA) incorporated into a variety of lipid vesicles/adjuvants. At each injection, the mice received 25 µg BSA. Mice were injected i.p. at days 0, 10 and 52, and sera collected 4 days after the second and third injections. Archaeosomes were prepared from the TPL extracted from the indicated archaeobacterium. Sera diluted 1:400. Vesicle/adjuvant composition (mg lipid/boost): BSA—no adjuvant or vesicle, BSA diluted in PBS; FA-BSA emulsified in Freund's adjuvant; *T. acidophilum* (0.75 mg); *M. mazei* (0.64 mg); *M. smithii* (0.57 mg); *M. voltae* (1.83 mg); *M. hungatei* (1.09 mg); *M. concilii* (0.68 mg); *M. stadtmanae* (0.51 mg); PC:PG (DMPC:DMPG, 2.11 mg); PC:PG:CHOL (DMPC:DMPG:CHOL, 0.12 mg); and PC:DCP:CHOL (DMPC:DCP:CHOL, 0.87 mg). Data are the means from mice in duplicates.

A comparison of the adjuvant/antigen carrier properties of archaeosomes and of conventional liposomes was made using BSA as the antigen (FIG. 8). The immune response to BSA was markedly enhanced when it was encapsulated in archaeosomes, and the results were again comparable, in some cases, to that achieved with Freund's adjuvant. In contrast, all three conventional liposome types yielded substantially lower immunostimulatory effects.

Figure 9:
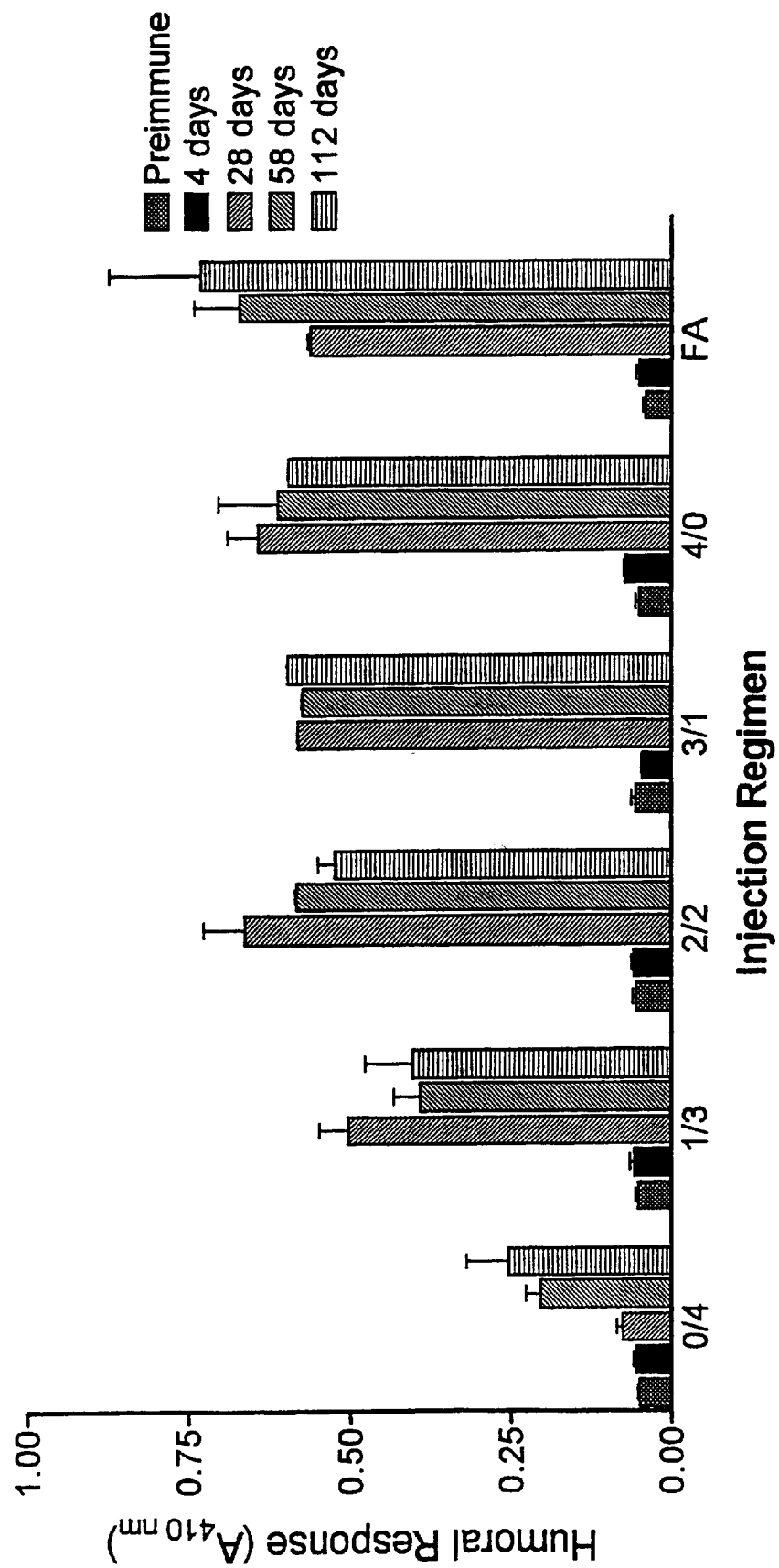
FIG. 9. Relationship between the number of immunizations with BSA encapsulated in archaeosomes and the resultant anti-BSA antibody titres in mouse sera. Each mouse received 25 µg BSA per i.p. injection either as bare antigen, encapsulated in *M. smithii* archaeosomes (0.58 mg lipid), or emulsified in FA. Mice were injected at days 0, 24, 54 and 108. Sera diluted 1:400. Injection regimen: 0/4, immunized up to 4 times with the bare antigen; 1/3, first injection with encapsulated antigen and remaining 3 boosts with the bare antigen; 2/2, first 2 injections with encapsulated antigen and remaining 2 boosts with the bare antigen; 3/1, first 3 injections with encapsulated antigen and remaining boost with the bare antigen; 4/0, 4 injections with encapsulated antigen; and FA, first injection with CFA, second with IFA, remaining 2 boosts with the bare antigen. Data are expressed as the means for duplicate mice.

The number of boosts needed to achieve a circulating antibody titre comparable to that achieved with Freund's adjuvant, was determined using the BSA antigen entrapped in archaeosomes of *M. smithii* (FIG. 9). When archaeosomes (with the antigen encapsulated) were given only once, followed by a boost with bare antigen, a considerable immune response, comparable to that with Freund's adjuvant, was achieved.

It was noted that the stimulation of the immune response with certain archaeosomes (for example *M. espanolae*)

administered i.p. required that the BSA antigen be entrapped in the vesicle, whereas with other archaeosomes (for example *T. acidophilum*) entrapment was not a prerequisite (Table 8). In another example using Cholera toxin B, the immunostimulatory effect was greater when the antigen was entrapped in the archaeosome (FIG. 7). However, when the BSA antigen was administered via the i.m. route, association with the archaeosome was required for a good immune response (Table 9). Hence, whether or not the antigen needed to be entrapped or associated with the vesicle would depend on the route of administration and the lipid composition of the vesicles.

For use in humans, other mammals, and other life-forms such as avian and marine species, it is important to obtain the immune reaction following immunization via normally acceptable routes of delivery. Comparison of s.c., i.m., and i.p. immunizations established that the humoral response could be elevated by archaeosomes administered via various routes (Table 10).

The small adjuvant effect observed with DMPC:DMPG conventional liposomes can be improved by the inclusion of increasing amounts of archaeobacterial lipids in the lipids used for vesicle formation. This is illustrated in Table 11 using vesicles made with DMPC:DMPG:*M. smithii* TPL, where the amount of TPL was varied from 0 to 100% in the mixture used to form vesicles and encapsulate the BSA antigen. An enhancement of the humoral immune response to the protein was seen by the inclusion into the vesicles of as little as 10% of archaeobacterial lipids, and progressive improvements seen up to 100%.

It is further shown that archaeosomes may be prepared from lipids obtained in a biologically pure form from archaeobacteria, and that these archaeosomes also have the ability to enhance the immune response to an antigen (Table 12). While all archaeosomes prepared from pure lipids produced a positive adjuvant effect, PGP-Me was superior. This may be explained by the novelty of the doubly charged anionic head group of PGP-Me.

The duration of the immune response to the encapsulated antigen is maintained longer when tetraether lipids are used, compared to diether lipids, to prepare the archaeosomes (Table 12). The decline in the antibody titre between 35 and 55. days was 40 to 46% in the case of Freunds adjuvant and the 3 diether lipid archaeosomes, whereas the decline was only 25% for the tetraether archaeosome.

Comparison of *M. smithii* archaeosomes prepared from the total lipid extract (includes neutral lipids) with those prepared from the total polar lipid extract (neutral lipids removed), established that the immune response to BSA. (anti-BSA antibody titres) administered i.p. was 63 and 91% respectively, of that found with Freund's adjuvant The amount of antigen administered, the immunization protocols and antibody titres were conducted as detailed in Table 11.

Figure 10:
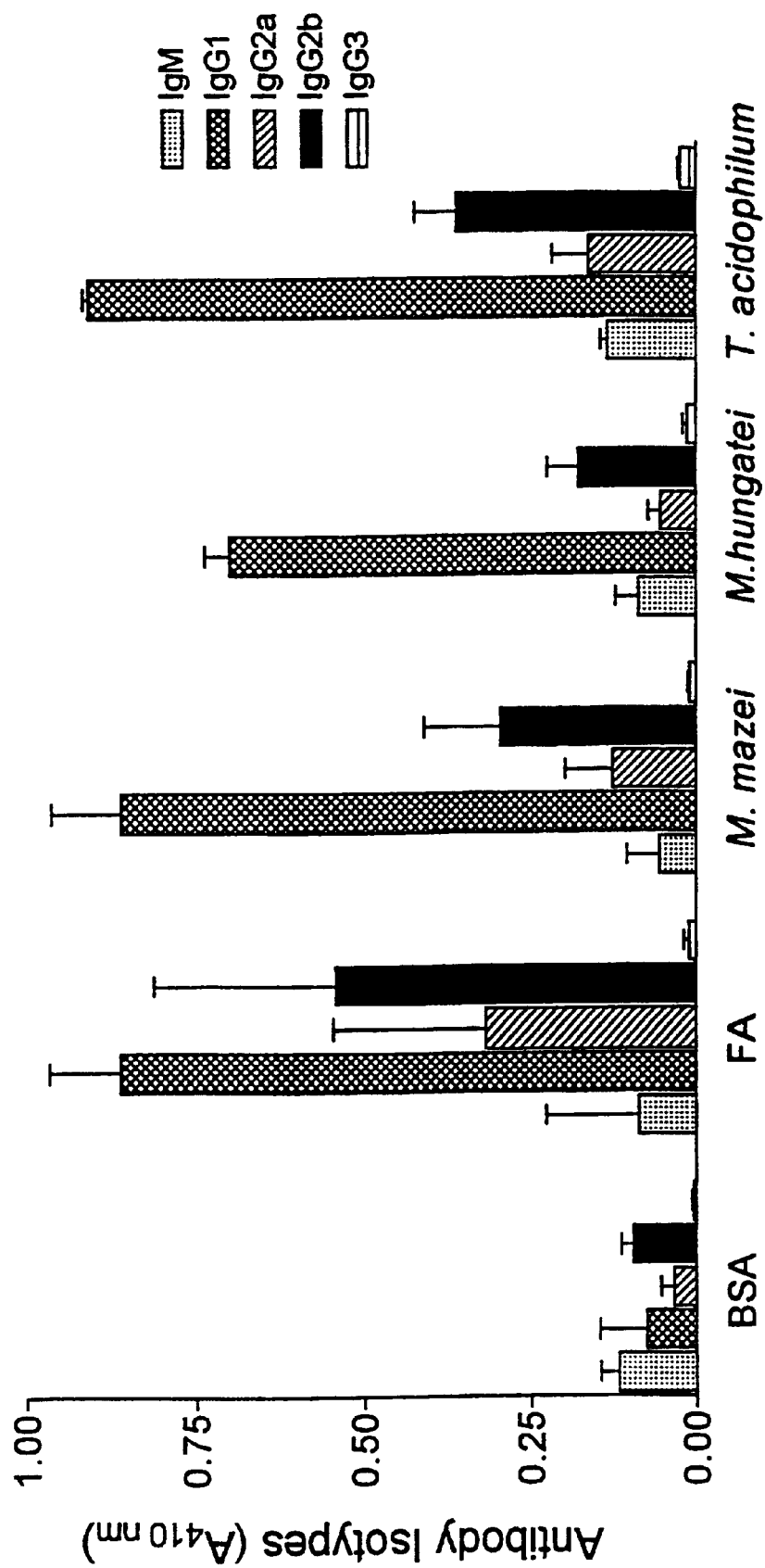
FIG. 10. Anti-BSA antibody isotypes found in mouse sera following immunizations with BSA encapsulated in archaeosomes. Injections were given i.m. to mice at days 0 and 14, using 12.5 µg BSA/injection. Archaeosomes carrying 12.5 µg BSA, prepared from the TPL, correspond to dry weights/injection of 0.69 mg (*M. mazei*), 0.55 mg (*M. hungatei*), and 1.5 mg (*T. acidophilum*). Sera samples were obtained on day 25 post first injection. Also shown are isotyping results for injections of bare BSA (BSA) and BSA with Freund's adjuvant (FA).

Archaeosomes with encapsulated/associated BSA elicited antibodies of various isotypes (FIG. 10) when administered to mice. The presence of IgG isotypes of the 2a/2b class are important indicators of protective immunity and of a cell-mediated immune reaction. Hence, archaeosomes elicit not only a humoral response to the antigen being carried, but also a cell-mediated response is expected.

Mice were immunized (days 0 and 14), i.p., with conventional liposomes (DSPC:DCP:CHOL) containing 15 µg BSA per dose, with and without $Q_{10}$ incorporated (see Table 5 and 6B for compositions). Sera collected on day 18 when titred for antibodies (IgG+IgM) had a significantly higher anti-BSA antibody titre (at the 95% confidence limit) when the liposomes contained $CoQ_{10}$.

Carbohydrates are known to be poor immunogens even when administered with known adjuvants. In addition to enhancing the immune response to protein antigens, it is shown here that the O-chain polysaccharide antigen from *E. coli* 0:157:H7 is immunogenic when associated with *M. smithii* archaeosomes. For these studies, Balb/c mice received 50 µg/injection (i.p.) of bare O-chain polysaccharide or 50 µg/injection of the same antigen encapsulated into 0.1 mg of *M. smithii* archaeosomes (TPL). One injection was given on day zero and blood collected on day 18 for titration of IgG+IgM antibodies. The bare antigen produced an $A_{410\ nm}$ reading of 0.004 compared to 0.231 with archaeosomes, representing an increase of about 58-times.

The dramatic increase in the immune response to antigens associated with archaeosomes, observed in this study, was unexpected and contrary to the expectations suggested from prior art disclosures using ether lipids. Indeed, Shek et al. (17) showed that vesicles made with dialkyl-ether phosphatidylcholines, with BSA as the entrapped antigen, were less efficient in eliciting an immune response in mice compared to liposomes made with the diacyl-ester phosphatidylcholine. In addition to enhanced adjuvant effects, few boosts are required with archaeosomes. Moreover, the storage stability (shelf life) of archaeosomes is long (20).

In vitro cytotoxicity studies with several phagocytic and non phagocytic cell lines described earlier indicated that neither archaeosomes nor conventional liposomes had any significant adverse effects, as assessed from cell viability assays, even when the vesicles were tested at lipid concentrations well above saturation. In mouse models, there were no signs of gross toxicities such as granulomas at sites of injection, gross changes in the key body organs or deaths. Anti-archaeosome lipid antibodies are not detected in the mouse sera obtained in FIG. 8. Further, there are indications that molecules with ether bonds can be slowly metabolised and eliminated from the body (21). The in vitro phagocytosis data presented in our disclosure also indicate that archaeosomes are at least sufficiently destabilized/degraded in the macrophages to release entrapped protein and fluorescent dye markers. The in vivo data on immune response also support that the archaeosomes containing encapsulated antigens are destabilized/degraded to allow presentation of the antigen to the antigen processing cells of the immune system.

REFERENCES

1. Allison, A. C., and Gregoriadis, G. (1977) Immunological preparations. U.S. Pat. No. 4,053,585.
2. Alving, C. R., Koulchin, V., Glenn, G. M., and Rao, M. (1995) Liposomes as carriers of peptide antigens: induction of antibodies and cytotoxic T lymphocytes to conjugated and unconjugated peptides. Immunological Rev. 145: 5–31.
3: Casey, A. C., and Bliznakov, E. G. (1972) Effect and structure-activity relationship of the coenzymes Q on the phagocytic rate of rats. Chem.-Biol. Interactions, 5: 1–12.
4. Estis, L., and Livingston, P. (1991) Adjuvant composition. U.S. Pat. No. 5,026,557.
5. Folkers, K., Langsjoen, P., Nara, Y., Muratsu, K., Komorowski, J., Richardson, P. C., and Smith, T. H. (1988) Biochemical deficiencies of coenzyme $Q_{10}$ in HIV-infection and exploratory treatment. Biochem. Biophys. Res. Commun. 153: 888–896.
6. Hrckova, G., Shah, A., Hart, D. T., and Halton, D. W. (1994) A comparative study of the utilization of ether- and ester-linked phospholipid-containing liposomes by J774.E1 macrophage cell-line infected with *Leishmania mexicana mixicana* amastigotes. Folia Parasitologica, 41:161–167.

7. Ishiwata, K., Miura, Y., Takahashi, T., Kawashima, K., Yanai, K., Monma, M., and Ido, T. (1985) $^{11}$C-Coenzyme $Q_{10}$: a new myocardial imaging tracer for positron emission tomography. Eur. J. Nud. Med. 11: 162–165.
8. Kates, M. (1993) Archaebacterial lipids: structure, biosynthesis and function. Biochem. Soc. Symp. 58: 51–72.
9. Kates, M., Moldoveanu, N., and Stewart, L. C. (1993) On the revised structure of the major phospholippid of *Halobacterium salinarium*. Biochim. Biophys. Acta 1169: 46–53.
10. MacDonald, R. C., MacDonald, R. I., Menco, B.PhM., Takeshita, K., Subbarao, N. K., and Hu, L. (1991) Small-volume extrusion apparatus for preparation of large, unilamellar vesicles. Biochim. Biophys. Acta 1061: 297–303.
11. Makabi-Panzu, B., Lessard, C., Beauchamp, D., Désormeaux, A., Poulin, L., Tremblay, M., and Bergeron, M. G. (1995) Uptake and binding of liposomal 2',3'-dideoxycytidine by RAW 264.7 cells: a three step process. J. Acquired Immune Deficiency Syndromes and Human Retrovirology 8: 227–235.
12. Makabi-Panzu, B., Lessard, C., Perron, S., Desormeaux, A., Tremblay, M., Poulin, L., Beauchamp, D., and Bergeron, M. G. (1994) Comparison of cellular accumulation, tissue distribution, and anti-HIV activity of free and liposomal 2',3'-dideoxycytidine. Aids Research and Human Retroviruses 11: 1463–1470.
13. New, R. R. C. (1990) Preparation of liposomes. In: R. R. C. New (ed.) Liposomes: A Practical Approach. I.R.L. Press, Oxford, pp. 33–104.
14. New, R. R. C. (1990) Characterization of liposomes. In: R. R. C. New (ed.) Liposomes: A Practical Approach. I.R.L. Press, Oxford, pp. 105–161.
15. New, R. R. C., Black, C. D. V., Parker, R. J., Puri, A., and Scherphof, G. L. (1990) Liposomes in biological systems. In: R. R. C. New (ed.) Liposomes: A Practical Approach. I.R.L. Press, Oxford, pp. 221–252.
16. Perry, M. B., MacLean, L., and Griffith, D. W. (1985) Structure of the O-chain polysaccharide of *Escherichia coli* 0:157:H7. Biochem. Cell Biol. 64: 21–28.
17. Shek, P. N., Yung, B. Y. K., and Stanacev, N. Z. (1986) Physicochemical and immunological properties of albumin-associated dialkyl-ether phosphatidylcholine liposomes. Biochim. Biophys. Acta 855: 33–40.
18. Sprott, G. D. (1992) Structures of Archaeobacterial membrane lipids. J. Bioenerget. Biomembr. 24: 555–566.
19. Sprott, G. D., Dicaire, C. J., and Patel, G. B. (1994) The ether lipids of *Methanosarcina mazei* and other Methanosarcina species, compared by fast atom bombardment mass spectrometry. Can. J. Microbiol. 40: 837–843.
20. Sprott, G. D., Patel, G. B., Choquet, C. G., and Ekiel, I. (1993) Formation of stable liposomes from lipid extracts of Archaeobacteria (Archaea). International Application No. PCT/CA92/00464, International Publication Number WO 93/08202.
21. Stein, Y., Halperin, G., Leitersdorf, E., Dabach, Y., Hollander, G., and Stein, O. (1984) Metabolism of liposomes prepared from a labelled ether analog of 1,2-dioleoyl-sn-glycero-3-phosphocholine in the rat Biochim. Biophys. Acta, 793: 354–364.
22. Takada, M., Yuzuriha, T., Katayama, K., Iwamoto, K., and Sunamoto, J. (1984) Increased lung uptake of liposomes coated with polysaccharides. Biochim. Biophys. Acta, 802: 237–244.
23. Tolson, D. L., Turco, S. J. and Pearson, T. W. (1990) Expression of a repeating phosphorylated disaccharide lipophosphoglycan epitope on the surface of macrophages infected with *Leishmania donovani*. Infect. Immun. 58: 3500–3507.
24. Woodle, M. C., Matthay, K. K., Newman, M. S., Hidayat, J. E., Collins, L. R., Redemann, C., Martin, F. J., and Papahadjopoulos, D. (1992) Versatility in lipid compositions showing prolonged circulation with sterically stabilized liposomes. Biochim. Biophys. Acta 1105: 193–200.

TABLE 1

Characteristics of peroxidase-archaeosomes and peroxidase-liposomes used in binding assays.[1]

| Lipid source for vesicles | Mean Diameter (nm ± standard deviation) | Peroxidase Activity[2] | |
|---|---|---|---|
| | | No Detergent | OGP |
| M. mazei | 189 ± 63 | 7.7 | 32.3 |
| M. hungatei | 218 ± 73 | 4.9 | 39.2 |
| M. jannaschii | 192 ± 69 | 3.5 | 34.7 |
| M. stadtmanae | 170 ± 63 | 10.3 | 31.6 |
| M. smithii | 200 ± 77 | 4.3 | 32.9 |
| M. voltae | 206 ± 65 | 3.3 | 26.3 |
| T. acidophilum | 184 ± 85 | 4.1 | 70.4 |
| DPPC | 324 ± (84)[3] | 1.4 | 48.4 |
| DMPC:DMPG:CHOL | 204 ± 72 | 0.69 | 31.8 |

[1]Pressure extruded vesicles were prepared from conventional lipids or from the total polar lipids of Archaeobacteria: *Methanosarcina mazei, Methanospirillum hungatei, Methanococcus jannaschii, Methanosphaera stadtmanae, Methanobrevibacter smithii, Methanococcus voltae,* and *Thermoplasma acidophilum*.
[2]Activity is expressed as change in absorbency/min/mg dry wt vesicles.
[3]Consisting of two populations of liposomes of 324 nm (84%, number weighted) and 2833 nm (16%, number weighted).

TABLE 2

Comparative in vitro uptake ($\mu$g/mg cell protein) of archaeosomes and conventional liposomes to murine peritoneal macrophages and a variety of cell lines.[1]

| Lipid source for vesicles | Murine Peritoneal Macrophages | J774A.1 Macrophages | HEp-2 cells | HeLa cells | EJ/28 cells |
|---|---|---|---|---|---|
| M. mazei | 36.4 ± 0.3 | 32.3 ± 0.6 | 3.5 ± 0.3 | 1.7 ± 0.1 | 1.3 ± 0.3 |
| M. hungatei | 32.9 ± 1.7 | 21.3 ± 1.2 | 0.7 ± 0.0 | 0.2 ± 0.0 | 1.3 ± 0.1 |
| M. jannaschii | 34.9 ± 3.0 | 24.6 ± 0.3 | 0.2 ± 0.0 | 1.4 ± 0.1 | 2.2 ± 0.1 |
| M. stadtmanae | 19.8 ± 0.5 | 20.4 ± 0.5 | 2.3 ± 0.3 | 1.4 ± 0.1 | 2.1 ± 0.0 |
| M. smithii | 43.2 ± 1.8 | 38.6 ± 1.4 | 1.1 ± 0.1 | 0.3 ± 0.0 | 2.3 ± 0.1 |

TABLE 2-continued

Comparative in vitro uptake (μg/mg cell protein) of archaeosomes and conventional liposomes to murine peritoneal macrophages and a variety of cell lines.[1]

| Lipid source for vesicles | Murine Peritoneal Macrophages | J774A.1 Macrophages | HEp-2 cells | HeLa cells | EJ/28 cells |
|---|---|---|---|---|---|
| M. voltae | 33.8 ± 0.2 | 23.8 ± 0.4 | 2.5 ± 0.0 | 1.2 ± 0.0 | 1.9 ± 0.1 |
| T. acidophilum | 13.5 ± 3.3 | not done | 0.7 ± 0.5 | 0.4 ± 0.3 | 1.1 ± 0.6 |
| DPPC | 0.8 ± 0.1 | 2.7 ± 0.1 | 0.6 ± 0.0 | 0.3 ± 0.0 | 1.1 ± 0.1 |
| DMPC:DMPG:CHOL | 6.0 ± 0.3 | 7.2 ± 0.2 | 0.2 ± 0.0 | 0.4 ± 0.0 | 2.1 ± 0.0 |

[1]Peroxidase-vesicles were assayed for binding to cell lines adhered to culture wells. For comparison purposes, the extent of colour reaction was corrected for the amount of enzyme entrapped within each vesicle preparation. Absorbency values were corrected by subtracting a blank obtained by adding all reagents to blank wells (no cells). Values are the average of duplicate samples ± sample standard deviation.

TABLE 3

Relative uptake of archaeosomes and conventional liposomes by various cell lines.[1]

| Lipid source for vesicles | Mean Diameter (nm ± standard deviation) | Vesicles added per assay well (μg) | Fluorescence[2] | Relative Binding[3] J774A.1 cells | HEp-2 cells | HeLa cells | EJ/28 cells |
|---|---|---|---|---|---|---|---|
| M. mazei | 143 ± 60 | 120 | 0.153 | 10 | 1 | 1 | 1 |
| M. espanolae | 205 ± 71 | 88 | 0.136 | 10 | 1 | 2 | 2 |
| DMPC:DMPG:CHOL | 223 ± 84 | 134 | 0.235 | 3 | 1 | 1 | 1 |

[1]Vesicles contained CF.
[2]Emission from 10 μl vesicles diluted into 190 μl PBS, to indicate the relative fluorescence of vesicle suspensions used in the uptake assays. Fluorescence was enhanced only 5 to 12% in the presence of 0.5% OGP.
[3]Assessed by fluorescence microscopy, where intense fluorescence from vesicles adhered to the cells is given a value of 10, and very weak background fluorescence is shown as 1.

TABLE 4

The effect of inhibitors on the phagocytosis of M. hungatei archaeosomes by J774A.1 macrophages.[1]

| Treatment | Relative binding/degradation of liposomes by macrophages at different intervals (min)[2] | | | | | | | |
|---|---|---|---|---|---|---|---|---|
| | 0 | 30 | 60 | 120 | 180 | 240 | 300 | 360 |
| None | 10 | 8 | 5 | 3 | 2 | 1 | N/D | N/D |
| Cytochalasins B + D | 10 | 10 | 10 | 8 | 8 | 7 | N/D | N/D |
| DMSO | 10 | 10 | 5 | 2 | 2 | 1 | N/D | N/D |
| Formaldehyde | 10 | 10 | 10 | 10 | 10 | 10 | N/D | N/D |
| 4° C. | 10 | 10 | 10 | 10 | 10 | 10 | N/D | N/D |
| 4 C. → 37° C.[3] | 10 | 10 | 10 | 10 | 7 | 5 | 2 | 1 |

[1]Archaeosomes with entrapped CF were prepared by pressure extrusion of the total polar lipids from M. hungatei. N/D, not determined.
[2]Assessed by fluorescence microscopy, where intense fluorescence is given a value of 10 and weak background fluorescence is 1.
[3]Temperature shifted to 37° C. at 120 min.

TABLE 5

Incorporation of coenzyme $Q_{10}$ into M. mazei archaeosomes and conventional liposomes.[1]

| Lipid source for vesicles | Starting ratio $Q_{10}$:lipid (mg:mg) | $Q_{10}$ Entrapment (%) | Loading Ratio (mg $Q_{10}$/mg lipid) |
|---|---|---|---|
| M. mazei | 5:20 | 62.1 ± 1.1 | 0.155 |
| DPPC:CHOL (5:5, molar ratio) | 5:20 | 91.5 ± 1.1 | 0.230 |
| DSPC:CHOL (5:5, molar ratio) | 5:20 | 86.1 ± .085 | 0.215 |
| DSPC:CHOL:DCP (4:5:1, molar ratio) | 5:20 | 53.7 ± 1.7 | 0.135 |

[1]Vesicles were prepared by REV-bath sonication, and were of an average diameter of 100 nm. The same lipid compositions were used for Tables 6–7. The % entrapment and the loading ratio were calculated from the starting amounts of $Q_{10}$ and lipids. A 100 % recovery of the lipids was assumed.

TABLE 6A

Uptake of *M. mazei* archaeosomes and conventional liposomes by J774A.1 macrophages as a function of time, using $^3$H-chol as the marker.[1]

| Lipid source for vesicles | Uptake (cpm)[2] | | | |
|---|---|---|---|---|
| | 15 min | 30 min | 45 min | 60 min |
| *M. mazei* | 1786 ± 80 | 2737 ± 92 | 2957 ± 247 | 3570 ± 68 |
| DPPC:CHOL | 290 ± 48 | 367 ± 39.4 | 430 ± 70 | 334 ± 73 |
| DSPC:CHOL | 259 ± 9 | 311 ± 23 | 643 ± 108 | 228 ± 25 |
| DSPC:CHOL:DCP | 570 ± 89 | 603 ± 25 | 694 ± 222 | 589 ± 28 |

[1]The values were determined by incubating cells with 25 μM of vesicles for the indicated incubation times. An average molecular weight of 1000 was used to calculate the moles of lipids of *M. mazei*. Each culture well received a total volume of 5 ml; 260, 500 cpm in 125 nmoles vesicles (Tables 6–7).
[2]cpm of accumulated lipid per mg of macrophage protein (± sample standard deviation, n = 3).

TABLE 6B

Influence of coenzyme $Q_{10}$ on the uptake of *M. mazei* archaeosomes and conventional liposomes by J774A.1 macrophages as a function of time, using $^3$H-chol as a marker.[1]

| Lipid source for vesicles | Uptake (cpm)[2] | | | |
|---|---|---|---|---|
| | 15 min | 30 min | 45 min | 60 min |
| *M. mazei* + $Q_{10}$ | 5009 ± 617 | 11979 ± 2198 | 10273 ± 545 | 51378 ± 6531 |
| DPPC:CHOL + $Q_{10}$ | 1770 ± 340 | 1385 ± 169 | 1958 ± 232 | 2589 ± 182 |
| DSPC:CHOL + $Q_{10}$ | 1369 ± 543 | 1453 ± 239 | 1599 ± 150 | 2280 ± 230 |
| DSPC:CHOL:DCP + $Q_{10}$ | 3450 ± 300 | 3538 ± 173 | 2314 ± 3 | 3241 ± 254 |

[1]The values were determined by incubating cells with 25 μM of vesicles for the indicated incubation times.
[2]cpm of accumulated lipid per mg macrophage protein (± sample standard deviation, n = 3).

TABLE 7A

Uptake of *M. mazei* archaeosomes and conventional liposomes by J774A.1 macrophages as a function of lipid concentration, using $^3$H-chol as a marker.[1]

| Lipid source for vesicles | Lipid concentration | | | |
|---|---|---|---|---|
| | 25 μM | 50 μM | 75 μM | 100 μM |
| *M. mazei* | 3011 ± 642[2] | 14487 ± 3696 | 7930 ± 773 | 10140 ± 1412 |
| DPPC:CHOL | 364 ± 83 | 1680 ± 572 | 1332 ± 300 | 1961 ± 241 |
| DSPC:CHOL | 255 ± 138 | 1961 ± 349 | 1323 ± 205 | 2049 ± 94 |
| DSPC:CHOL:DCP | 365 ± 138 | 4246 ± 232 | 3147 ± 618 | 3755 ± 44 |

[1]The values were determined after incubating cells for 60 min with the indicated lipid concentrations.
[2]Data are shown as cpm of accumulated lipid/mg protein (± sample standard deviation, n = 3).

TABLE 7B

Influence of coenzyme $Q_{10}$ on the uptake of *M. mazei* archaeosomes and conventional liposomes by J774A.1 macrophages as a function of lipid concentration, using $^3$H-chol as a marker.[1]

| Lipid source for vesicles | Lipid concentration | | | |
|---|---|---|---|---|
| | 25 μM | 50 μM | 75 μM | 100 μM |
| *M. mazei* + $Q_{10}$ | 27598 ± 190[2] | 44558 ± 1642 | 32671 ± 7762 | 23711 ± 3518 |
| DPPC:CHOL + $Q_{10}$ | 3497 ± 303 | 7743 ± 1792 | 10220 ± 3174 | 14195 ± 6225 |
| DSPC:CHOL + $Q_{10}$ | 2716 ± 691 | 6499 ± 1400 | 12389 ± 1311 | 9226 ± 341 |
| DSPC:CHOL:DCP + $Q_{10}$ | 3203 ± 425 | 20411 ± 828 | 10290 ± 4270 | 13228 ± 2500 |

[1]The values were determined after incubating cells for 60 min with the indicated vesicle lipid concentrations.
[2]cpm of accumulated lipid/mg protein (± sample standard deviation, n = 3).

TABLE 8

Influence of encapsulation of the antigen delivered i.p. on the effectiveness of various archaeosomes to increase a humoral immune response.[1]

| Carrier/adjuvant | Diameter (nm) | Archaeosome (mg/injection) | Encapsulation of Antigen | Antibody titre ($A_{410\ nm}$) | Concentration (μg/ml) |
|---|---|---|---|---|---|
| *M. espanolae* | 190 ± 61 | 0.58 | Yes | 0.536 ± 0.141 | 41.2 |
| *M. espanolae* | 191 ± 60 | 0.58 | No | 0.108 ± 0.002 | 8.3 |
| *M. espanolae* | 191 ± 60 | 0.58 | No antigen | 0.018 ± 0.000 | 1.4 |
| *T. acidophilum* | 245 ± 94 | 1.04 | Yes | 0.385 ± 0.019 | 29.6 |
| *T. acidophilum* | 273 ± 84 | 1.04 | No | 0.443 ± 0.016 | 34.1 |
| *M. smithii* | 173 ± 77 | 2.42 | Yes | 0.580 ± 0.044 | 44.6 |
| *M. smithii* | 201 ± 65 | 2.42 | No | 0.258 ± 0.016 | 19.9 |
| *M. mazei* | 159 ± 61 | 1.10 | Yes | 0.656 ± 0.074 | 50.5 |
| *M. mazei* | 130 ± 64 | 1.10 | No | 0.405 ± 0.054 | 31.2 |
| *M. mazei* | 130 ± 64 | 1.10 | No antigen | 0.031 ± 0.005 | 2.4 |
| *M. hungatei* | 218 ± 69 | 1.2 | Yes | 0.297 ± 0.059 | 22.9 |
| *M. hungatei* | 287 ± 62 | 1.2 | No | 0.342 ± 0.082 | 26.3 |
| Freund's | — | None | As emulsion | 0.615 ± 0.026 | 47.3 |
| None | — | None | Bare BSA | 0.137 ± 0.002 | 10.5 |

[1]25 μg of BSA antigen was given per injection i.p. to each mouse. Immunizations where antigen was not encapsulated consisted of BSA in PBS followed by bare liposomes 4 hours later. Bare BSA is a control for antigen alone in PBS. Immunizations were given at 0 and 14 days, with blood being taken 4 days following the last boost. ELISA absorbency data (IgG + IgM) are shown for sera diluted 400 fold, and represent the average and sample standard deviation for mice in triplicates, witheach serum sample assayed twice. Anti-BSA antibody concentrations are calculated from the antibody titre data to give μg/ml of undiluted sera.

TABLE 9

Influence of encapsulation of the antigen delivered i.m., on effectiveness of various archaeosome preparations to increase a humoral immune response.[1]

| Carrier/adjuvant | Archaeosomes (mg/injection) | Encapsulation of Antigen | Antibody titre ($A_{410\ nm}$) |
|---|---|---|---|
| *M. mazei* | 0.690 | Yes | 0.248 ± 0.056 |
| *M. mazei* | 0.690 | No | 0.100 ± 0.005 |
| *T. acidophilum* | 1.50 | Yes | 0.251 ± 0.099 |
| *T. acidophilum* | 1.50 | No | 0.100 ± 0.033 |
| *M. hungatei* | 0.553 | Yes | 0.107 ± 0.021 |
| *M. hungatei* | 0.553 | No | 0.071 ± 0.007 |
| Freund's | As emulsion | — | 0.450 ± 0.026 |
| None | Bare BSA | — | 0.063 ± 0.003 |

[1]12.5 μg of BSA antigen was given per i.m. injection to the rear haunch. Immunizations where antigen was not associated/encapsulated with the archaeosomes consisted of BSA in PBS injected into one haunch of the mouse and the bare archaeosome injected immediately thereafter into the other haunch. Bare BSA is antigen alone in PBS. Injections were at days 0 and 14, with blood taken 7 days following the last boost. ELISA data (IgG + IgM) are shown for sera diluted 400-fold and represent theaverage and sample standard deviations for mice in triplicates, with each serum sample assayed twice.

TABLE 10

Influence of injection route on the humoral response to BSA entrapped in *M. espanolae* archaeosomes.[1]

| Injection Route | Antibody titre ($A_{410\ nm}$) | Antibody concentration ($\mu$g/ml) |
|---|---|---|
| i.p. | 0.773 ± 0.109 | 118.9 |
| s.c. | 0.493 ± 0.065 | 75.8 |
| i.m. | 0.535 ± 0.066 | 82.3 |

[1]BSA entrapped in *M. espanolae* archaeosomes of 147 ± 59 nm diameter (25 $\mu$g BSA in 0.24 mg lipid/injection) was used to inject mice at days 0, and 14. Blood was taken on day 18. Antibody titres (IgG + IgM) are shown as the average and sample standard deviation for 3 mice, with each serum assayed in duplicate. Absorbency data are shown for sera diluted 800 fold; anti-BSA antibody concentrations are calculated as $\mu$g/ml of undiluted sera.

TABLE 11

Relationship between the percentage of archaeobacterial lipids used in the preparation of vesicles and their ability to serve as a carrier/adjuvant for an entrapped antigen.[1]

| Carried/Adjuvant | archaeobacterial lipids (%) | Diameter (nm) | Vesicles/ injection (mg) | Immune response (Relative %) |
|---|---|---|---|---|
| Freund's | none | — | — | 100 ± 7.0 |
| None | none | — | — | 6.9 ± 0.3 |
| Archaeosomes | 100 | 180 ± 81 | 1.19 | 91.4 ± 5.9 |
| Archaeosomes | 50 | 186 ± 57 | 0.86 | 44.0 ± 11.5 |
| Archaeosomes | 10 | 152 ± 54 | 1.14 | 22.4 ± 3.9 |
| Liposomes | 0 | 126 ± 56 | 1.01 | 9.8 ± 0.9 |

[1]Mice (3 per group) were immunized by i.p. injections of various adjuvants containing 12.5 $\mu$g of BSA, as antigen. Vesicles were prepared from different ratios by weight of TPL from *Methanobrevibacter smithii* (archaeobacterial lipids) and DMPC:DMPG. The dry weight of vesicles given per injection was calculated to deliver a constant amount of 12.5 $\mu$g antigen. Mice were immunized at days 0 and 14. Blood was taken at day 20, and the immune response determined as titres of IgG + IgM antibodies in the serum using the ELISA method.

TABLE 12

Humoral response to a protein antigen entrapped in archaeosomes prepared from purified archaeal lipids.[1]

| Adjuvants/ Carrier | Diameter (nm)[2] | | Antibody titres ($A_{410\ nm}$) | | |
|---|---|---|---|---|---|
| | Day 0 | Day 14 | Day 25 | Day 35 | Day 55 |
| None | — | — | 0.064 ± 0.001 | 0.082 ± 0.007 | 0.075 ± 0.008 |
| Freund's | — | — | 0.610 ± 0.072 | 0.606 ± 0.069 | 0.385 ± 0.066 |
| PGP-Me | 124 ± 54 | 137 ± 52 | 0.574 ± 0.090 | 0.540 ± 0.124 | 0.290 ± 0.088 |
| $D_{OH}PI$ | 140 ± 59 | 138 ± 58 | 0.232 ± 0.022 | 0.238 ± 0.051 | 0.143 ± 0.032 |
| $D_{OH}PG$ | 217 ± 71 | 192 ± 75 | 0.401 ± 0.107 | 0.332 ± 0.044 | 0.199 ± 0.020 |
| Tetraether | 229 ± 100 | 202 ± 103 | 0.338 ± 0.029 | 0.238 ± 0.028 | 0.178 ± 0.004 |

[1]12.5 $\mu$g BSA was injected i.p. per mouse at days 0 and 14. Blood was taken from the tail vein at the times indicated from first injection (25–55 days). Antibody absorbency data are shown for sera diluted by a factor of 400, and represent the average and sample standard deviation for triplicate mice, with each serum assayed twice.
[2]Vesicle diameters were determined at the time of the first (day 0) and second (day 14) injections.

We claim:

1. A liposome composition comprising (1) the total polar lipids extract of an archaeobacterium, (2) a pharmaceutical agent and (3) coenzyme $Q_{10}$.

2. A liposome composition according to claim 1, further comprising (4) a polyethyleneglycol lipid conjugate.

3. A liposome composition according to claim 1, wherein the archaeobacterium is selected from the group consisting of *Methanosarcina mazei*, *Methanospirillum hungatei*, *Methanosphaera stadtmanae*, *Methanobrevibacter smithii*, *Methanococcus voltae*, *Methanobacterium espanolae*, *Methanosaeta concilii*, and *Thermoplasma acidophilum*.

4. A liposome composition according to claim 1, wherein the liposome is unilamellar.

5. A liposome composition according to claim 1, wherein the liposome size is in the range of not less than 50 nm, but less than 500 nm, in diameter.

6. A liposome composition according to claim 1 wherein the archaeobacterium is *Methanosarcina mazei*.

7. A liposome composition according to claim 1, wherein the archaeobacterium is *Thermoplasma acidophilum*.

8. A method for the delivery of a pharmaceutical agent to an animal, comprising administering to the animal a liposome prepared from a composition consisting essentially of the total polar lipids extract of an archaeobacterium and coenzyme $Q_{10}$, as a carrier for said pharmaceutical agent.

9. A method for the delivery of a pharmaceutical agent to an animal, comprising administering to the animal a liposome prepared from a composition consisting essentially of the total polar lipids extract of an archaeobacterium, coenzyme $Q_{10}$, and a polyethyleneglycol lipid conjugate, as a carrier for said pharmaceutical agent.

10. A method according to claim 9, wherein the liposome is administered to an animal orally, intraperitoneally, intramuscularly, subcutaneously, or intravenously.

11. A method according to claim 9, herein the archaeobacterium is *Methanosarcina mazei*.

12. A method for enhancing the targeted delivery of a pharmaceutical agent to specific animal organs, comprising administering to the animal a liposome prepared from a composition consisting essentially of the total polar lipids extract of an archaeobacterium, coenzyme $Q_{10}$, and a polyethyleneglycol lipid conjugate, as a carrier for said pharmaceutical agent.

13. A method according to claim 12, wherein the liposome is delivered to an animal via the oral route.

14. A method for the delivery of a pharmaceutical or biological agent to phagocytic cells of an animal, comprising administering to the animal a liposome prepared from a composition consisting essentially of the total polar lipids extract of an archacobacterium as a carrier for said pharmaceutical or biological agent.

15. A method according to claim 14, wherein the pharmaceutical or biological agent is selected from an antibiotic, antiviral agent, vitamin, imaging agent, enzyme, DNA or hormone.

16. A method of treatment for a disease caused by a pathogen residing inside the cells of an animal, comprising administering to the animal a liposome prepared from the total polar lipids extract of an archaeobacterium and an antimicrobial or an antiviral agent.

17. A method of imaging of tissues and organs in an animal, comprising administering to the animal a liposome prepared from a composition consisting essentially of the total polar lipids extract of an archaeobacterium as a carrier for an imaging agent.

18. A method for the selective delivery of a pharmaceutical or biological agent to specific tissues of an animal, comprising administering to the animal a liposome prepared from a composition consisting essentially of the total polar lipids extract of an archaeobacterium and as a carrier for said pharmaceutical or biological agent.

19. A method according to claim 18, wherein the pharmaceutical or biological agent is selected from an antibiotic, antiviral agent, vitamin, imaging agent, enzyme, DNA or hormone.

20. A method according to claim 18, wherein the liposome composition additionally comprises a polyethyleneglycol lipid conjugate.

21. A method according to any one of claims 14, 15, 16, 17, 18, 19 or 20, wherein the archaeobacterium is selected from the group consisting of *Methanosarcina mazei, Methanospirillum hungatei, Methanosphaera stadtmanae, Methanobrevibacter smithii, Methanococcus voltae, Methanobacterium espanolae, Methanosaeta concilii* and *Thermoplasma acidophilum*.

22. A method according to any one of claims 14, 15, 16, 17, 18, 19 or 20, wherein the dosage of liposomes to be delivered is 4 to 73 mg/kg of animal body weight.

23. A method according to any one of claims 14, 15, 16, 17, 18, 19 or 20, wherein the archaeobacterium is *Methanosarcina mazei*.

24. A method according to any one of claim 14, 15, 16, 17, 18, 19 or 20, wherein the liposome is administered to an animal orally, intraperitoneally, intramuscularly, subcutaneously, or intravenously.

* * * * *